(12) United States Patent
Itsuji

(10) Patent No.: US 9,164,031 B2
(45) Date of Patent: Oct. 20, 2015

(54) MEASUREMENT APPARATUS AND METHOD, TOMOGRAPHY APPARATUS AND METHOD

(71) Applicant: CANON KABUSHIKI KAISHA, Tokyo (JP)

(72) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/372,418

(22) PCT Filed: Feb. 27, 2013

(86) PCT No.: PCT/JP2013/056060
§ 371 (c)(1),
(2) Date: Jul. 15, 2014

(87) PCT Pub. No.: WO2013/133294
PCT Pub. Date: Sep. 12, 2013

(65) Prior Publication Data
US 2015/0008324 A1    Jan. 8, 2015

(30) Foreign Application Priority Data
Mar. 4, 2012 (JP) ................................. 2012-047462

(51) Int. Cl.
*G01N 21/3586* (2014.01)
*G01N 21/3581* (2014.01)
(Continued)

(52) U.S. Cl.
CPC ............ *G01N 21/3586* (2013.01); *G01B 11/06* (2013.01); *G01N 21/35* (2013.01);
(Continued)

(58) Field of Classification Search
CPC ........................... G01N 21/35; G01N 21/3581
USPC ............................................. 250/338.1, 330
See application file for complete search history.

(56) References Cited

U.S. PATENT DOCUMENTS

| 7,498,577 B2 | 3/2009 | Kurosaka et al. |
| 7,531,804 B2 | 5/2009 | Itsuji |

(Continued)

FOREIGN PATENT DOCUMENTS

| EP | 2031374 A2 | 3/2009 |
| JP | 3602925 B2 | 12/2004 |

(Continued)

OTHER PUBLICATIONS

International Search Report and Written Opinion of the International Searching Authority issued in counterpart application No. PCT/JP2013/056060 dated Jun. 13, 2013—10 pages.

*Primary Examiner* — David Porta
*Assistant Examiner* — Meenakshi Sahu
(74) *Attorney, Agent, or Firm* — Fitzpatrick, Cella, Harper & Scinto

(57) ABSTRACT

An apparatus configured to obtain a physical property of an object by time-domain spectroscopy includes: a detection unit; a delay unit configured to adjust a time difference between generation and detection; a shaping unit configured to collect the electromagnetic wave pulses; a waveform obtaining unit configured to construct a time waveform of the electromagnetic wave pulses; and a collecting position adjusting unit configured to adjust a collecting position. When the collecting position is moved, an amount of adjustment when the collecting position matches first and second reflection portions, respectively, of the object, and a difference by the delay unit required for detecting first and second pulses of the time waveform are obtained, and from an amount of change of the amount of adjustment and the difference, a thickness and a refractive index of a region between the first and second reflection portions of the object are calculated.

20 Claims, 15 Drawing Sheets

(51) Int. Cl.
*G01N 21/35* (2014.01)
*G01B 11/06* (2006.01)
*G01N 21/41* (2006.01)
*G01N 21/47* (2006.01)

(52) U.S. Cl.
CPC ............ *G01N21/3581* (2013.01); *G01N 21/41* (2013.01); *G01N 21/47* (2013.01); *G01N 21/4795* (2013.01); *G01N 2201/0638* (2013.01); *G01N 2201/0697* (2013.01); *G01N 2201/06113* (2013.01)

(56) References Cited

U.S. PATENT DOCUMENTS

| | | | |
|---|---|---|---|
| 7,551,269 B2 | 6/2009 | Itsuji | |
| 7,619,736 B2 | 11/2009 | Itsuji | |
| 7,763,868 B2 | 7/2010 | Ouchi et al. | |
| 7,852,466 B2 | 12/2010 | Itsuji | |
| 7,994,478 B2 | 8/2011 | Kurosaka et al. | |
| 8,405,406 B2 | 3/2013 | Itsuji | |
| 2009/0059205 A1 | 3/2009 | Itsuji | |
| 2009/0231571 A1 | 9/2009 | Itsuji | |
| 2010/0171835 A1* | 7/2010 | Kasai et al. | 348/162 |
| 2010/0195090 A1 | 8/2010 | Ohtake | |
| 2011/0272579 A1 | 11/2011 | Itsuji | |
| 2013/0334421 A1 | 12/2013 | Itsuji | |

FOREIGN PATENT DOCUMENTS

| | | |
|---|---|---|
| JP | 4046158 B2 | 2/2008 |
| JP | 2010-181164 A | 8/2010 |
| WO | 2010/084765 A1 | 7/2010 |

\* cited by examiner

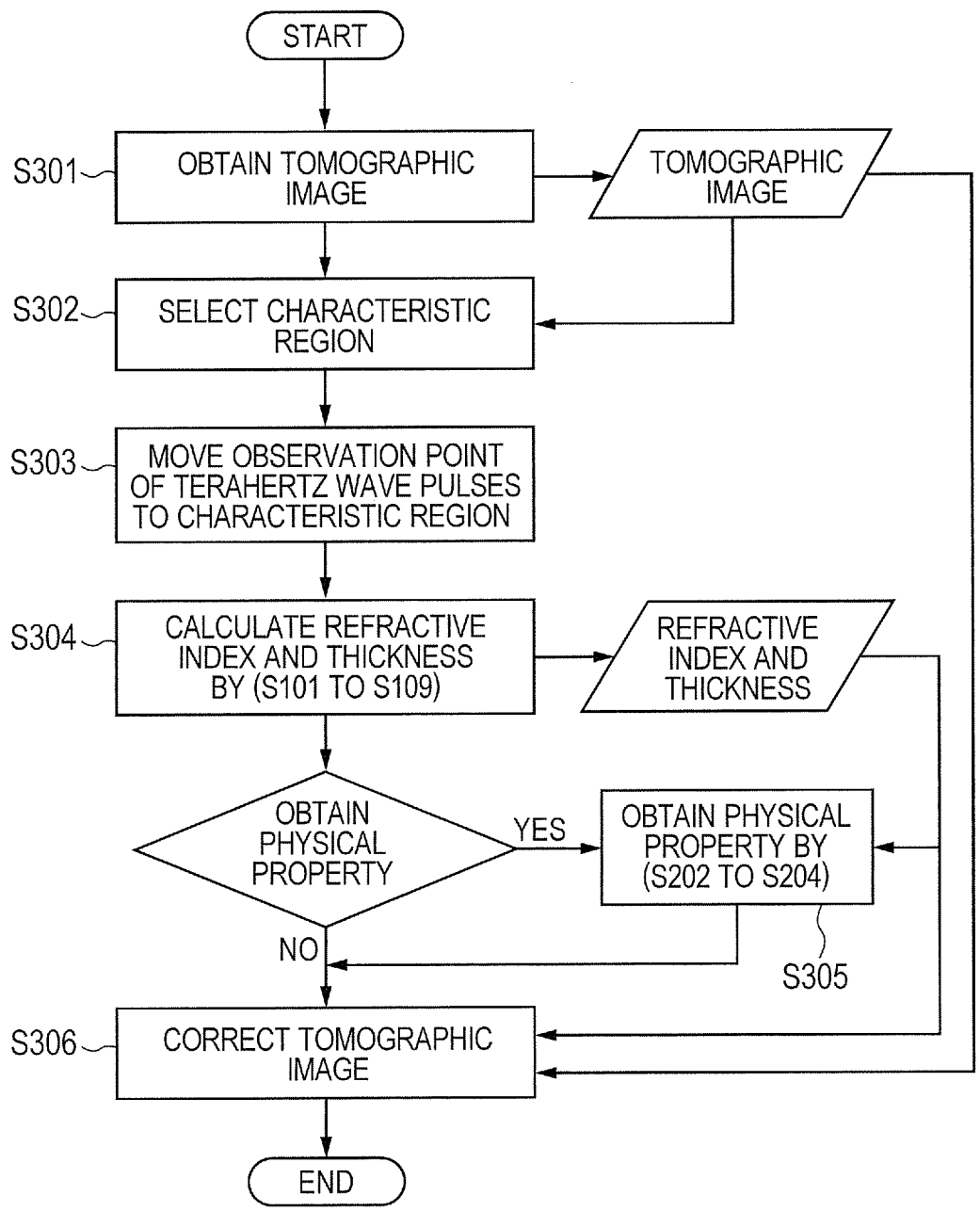

MEASUREMENT APPARATUS AND METHOD, TOMOGRAPHY APPARATUS AND METHOD

TECHNICAL FIELD

The present invention relates to a measurement apparatus and method using electromagnetic waves. The present invention also relates a tomography apparatus and method.

BACKGROUND ART

Terahertz waves typically are electromagnetic waves having components of any frequency bands within a range of 0.03 THz to 30 THz. Such frequency bands include many characteristic absorption bands derived from structures or states of various substances including biomolecules. Using such characteristics, inspection techniques of non-destructive analysis or identification of substances have been developed. Also, application of terahertz waves to safe imaging techniques replacing X-rays or high speed communication techniques is expected. Further, it is noted that reflection terahertz waves from a refractive index interface in an object to be measured are applied to a tomography apparatus configured to visualize an inside of the object to be measured. Such an apparatus is expected to visualize an inner structure at a depth of several hundreds of μm to several tens of mm using a characteristic of transmission of terahertz waves. In many cases, terahertz waves in the form of subpicosecond pulses are used for such use. Usually, it is difficult to obtain such pulses in an actual time. Thus, a THz-TDS apparatus (terahertz time-domain spectroscopy apparatus) performs sampling measurement using ultrashort pulsed lights (also herein referred to as excitation lights) having a femtosecond pulse width. Sampling of the terahertz waves is achieved by adjusting an optical path length difference between excitation lights reaching a generation unit configured to generate the terahertz waves and a detection unit configured to detect the terahertz waves. For example, the optical path length difference is adjusted according to an amount of fold of the excitation lights by inserting a stage (also herein referred to as a delay optical unit) having a folded optical system into propagation paths of the excitation lights. In many cases, a photoconductive element having an antenna electrode pattern with a minute gap provided on a semiconductor thin film is used as the generation unit or the detection unit.

In an example of the present invention, physical properties of an object to be measured are obtained using the principle of a THz-TDS apparatus. The physical properties of the object to be measured mainly include a refractive index and a shape (thickness) of the object to be measured. These physical properties are often calculated using terahertz wave pulses, from a time difference between reflection pulses from a refractive index interface of the object to be measured (see PTL 1). An interval between the reflection pulses corresponds to an optical length of propagation of terahertz waves. The optical length of the terahertz waves is expressed in the form of n(ave)×t by multiplying a thickness t of the object to be measured by an average refractive index n(ave). The average refractive index refers to a typical refractive index of the object to be measured. For example, the average refractive index refers to an average value of refractive index dispersion in a frequency band used. Otherwise, the average refractive index refers a refractive index at frequency (wavelength) having highest intensity in a frequency spectrum of the object to be measured. It is difficult to calculate the thickness t and the average refractive index n(ave) of the object to be measured from a measurement result of the terahertz waves because there is only one measurement result for two unknowns. To solve this problem, PTL 1 calculates a refractive index of an object to be measured by another unit. As such, to separate the thickness t and the average refractive index n(ave) from the measurement result, either of them needs to be obtained using another measurement unit. For this purpose, properties of the object to be measured are desirably specified to some degree before measurement. However, such an act may limit an application range as a measurement apparatus.

Meanwhile, for an OCT apparatus (Optical Coherence Tomography apparatus), some techniques for separating such information have been developed as described below. A confocal optical system is constructed, and a thickness t and an average refractive index n(ave) are simultaneously calculated from, an amount of movement of a focus in a collecting position of the confocal optical system in a depth direction of an object to be measured, and an amount of change of an optical path length difference of an interference system required for obtaining a maximum interference signal for each focus. Specifically, the thickness t and the average refractive index n(ave) of the object to be measured are calculated from a ratio of the amount of change of the optical path length difference to the amount of movement of the focus (see PTL 2).

CITATION LIST

Patent Literature

PTL 1: Japanese Patent No. 4046158
PTL 2: Japanese Patent No. 3602925

SUMMARY OF INVENTION

Technical Problem

In the above described technique in PTL 2, the ratio of the amount of change of the optical path length difference to the amount of movement of the focus in the collecting position is important, and thus a position of a refractive index interface connecting focuses needs to be accurately calculated. Since a wavelength used in the OCT apparatus is several μm or less, a depth of focus in the confocal optical system becomes several tens of μm. Thus, for an object to be measured having a thickness of several hundreds of μm to several tens of mm, the depth of focus is sufficiently small and a proper confocal optical system can be constructed. In other words, the focus of the optical system can be recognized as a point. This makes clear a boundary of the refractive index interface of the object to be measured, and provides high measurement accuracy of the thickness t and the average refractive index n(ave) of the object to be measured.

However, when the technique of PTL 2 is applied to a technique of using electromagnetic waves having a long wavelength such as terahertz waves, problems occur as described below. The terahertz waves have a long wavelength of several hundreds of μm, and provide a depth of focus of several mm when a confocal optical system is constructed. A beam in a region corresponding to the depth of focus, in view of wave-optics, propagates in a collimated shape with a minimum changes. The region where the beam propagates in a collimated shape in a collecting portion is herein referred to as a collimated region. In the technique of terahertz waves, the collimated region ranges several mm. Wave-optically, the confocal optical system includes a region where the beam is in a process of being collected (also herein referred to as a collecting process region) and the collimated region described above, and the system is often used on the assumption that the object to be measured is sufficiently larger than the collimated region. In the condition described above, it can be also said that the collimated region is a region with a reduced function of the confocal optical system. By analyzing the focus of the optical system in detail, the focus of the optical system is defined as a certain region rather than a point. If the object to be measured having substantially the same size as the collimated region is measured in the confocal optical system, an influence of the amount of movement of the focus is relatively increased. This makes unclear the boundary of the refractive index interface of the object to be measured, and it reduces measurement accuracy of the thickness t and the average refractive index n(ave) of the object to be measured. This phenomenon occurs when the object to be measured of substantially the same size as the collimated region in the confocal optical system is measured, with any wavelengths, not limited to the terahertz waves.

Solution to Problem

In view of the above, a measurement apparatus of the present invention configured to apply electromagnetic wave pulses to an object to be measured to obtain a physical property of the object to be measured including at least a first reflection portion and a second reflection portion by time-domain spectroscopy includes: a detection unit configured to detect the electromagnetic wave pulses from the object to be measured; a delay optical unit configured to adjust an optical path length difference between the electromagnetic wave pulses reaching the detection unit and an excitation light reaching the detection unit for detecting the electromagnetic wave pulses; a shaping unit configured to collect the electromagnetic wave pulses on the object to be measured; a waveform obtaining unit configured to refer to an output from the detection unit and an amount of adjustment of the optical path length difference by the delay optical unit to construct a time waveform of the electromagnetic wave pulses; a collecting position adjusting unit configured to adjust a relative position between the object to be measured and a collecting position; a measurement position information obtaining unit configured to obtain positions of the reflection portions of the object to be measured as an amount of adjustment by the collecting position adjusting unit, and an optical path length difference by the delay optical unit required for detecting a part of the time waveform of the pulses from the reflection portions at the amount of adjustment; and a physical property obtaining unit configured to obtain an amount of adjustment $Z_1$ by the collecting position adjusting unit when the collecting position of the electromagnetic wave pulses matches the first reflection portion of the object to be measured, an optical path length difference $D_1$ by the delay optical unit required for detecting a first pulse of the time waveform, an amount of adjustment $Z_2$ by the collecting position adjusting unit when the collecting position of the electromagnetic wave pulses matches the second reflection portion of the object to be measured, and an optical path length difference $D_2$ by the delay optical unit required for detecting a second pulse of the time waveform, which are obtained by the measurement position information obtaining unit, and calculate a thickness and a refractive index of a region between the first reflection portion and the second reflection portion of the object to be measured based on an amount of change $|Z_2-Z_1|$ of the amount of adjustment by the collecting position adjusting unit, and an amount of change $|D_2-D_1|$ of the optical path length difference by the optical delay portion.

Advantageous Effects of Invention

According to the present invention, even if the size of the region between the reflection portions of the object to be measured is close to the size of the collimated region of the electromagnetic wave pulses, the positions of the reflection portions can be accurately specified. This can increase detection accuracy of the thickness and the refractive index of the region between the first reflection portion and the second reflection portion. When terahertz wave pulses are used as the electromagnetic wave pulses, using transmission of the terahertz wave pulses allows visualization of an inner structure at a depth of several hundreds of μm to several tens of mm, and specification of the physical property.

Further features of the present invention will become apparent from the following description of exemplary embodiments with reference to the attached drawings.

BRIEF DESCRIPTION OF DRAWINGS

FIG. 14 illustrates an operation of the apparatus of Embodiment 4.

DESCRIPTION OF EMBODIMENTS

In the present invention, a position of a reflection portion (such as a refractive index interface) of an object to be measured is calculated from a change of a time waveform that follows a change of a collecting position of electromagnetic wave pulses with respect to the object to be measured. In use of terahertz wave pulses having a relatively long wavelength, the collecting position is typically a collimated region described later in a portion where the electromagnetic wave pulses are collected. A timing when the collecting position of the electromagnetic wave pulses matches first and second reflection portions of the object to be measured refers a timing when a light collecting process region described later of the electromagnetic wave pulses, an interface of the collimated region, and the first and second reflection portions of the object to be measured match.

Now, embodiments and examples of the present invention will be described. These relate to an apparatus and a method for calculating physical properties, for example, a refractive index and a thickness of a region between the first reflection portion and the second reflection portion of the object to be measured.

Embodiment 1

Figure 1:
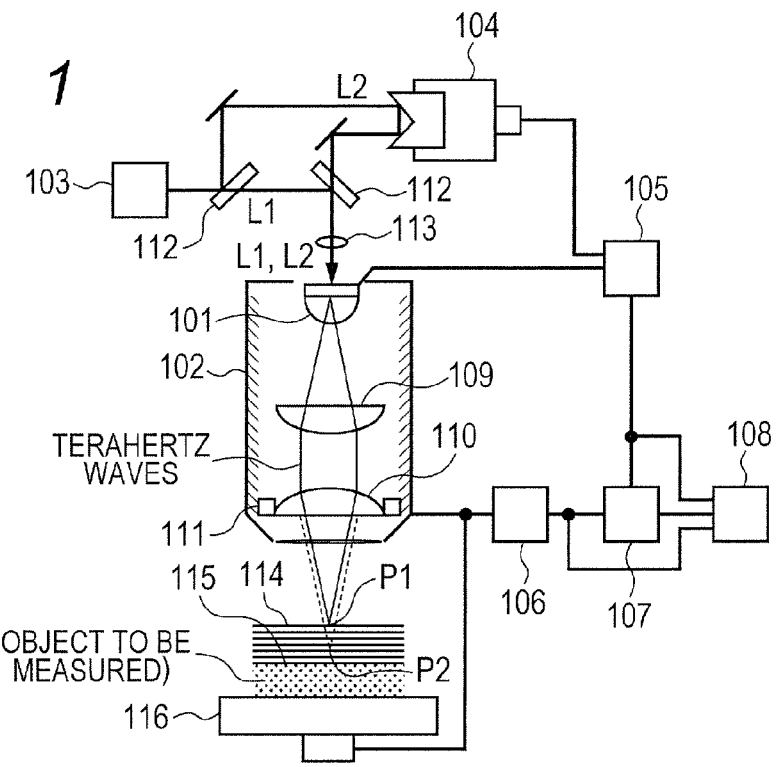
FIG. 1 is a schematic configuration diagram of an apparatus described in Embodiment 1.

An embodiment of the present invention will be described with reference to the drawings. FIG. 1 is a schematic configuration diagram of a physical property measurement apparatus of this embodiment. As shown in FIG. 1, the physical property measurement apparatus of this embodiment includes at least: a generation/detection unit 101 configured to generate and detect electromagnetic wave pulses, and a shaping unit 102 configured to shape and collect the electromagnetic wave pulses; a light source 103 configured to output an excitation light for the generation/detection unit 101 to generate and detect the electromagnetic wave pulses by; a delay optical unit 104 configured to adjust an optical path length difference between the electromagnetic wave pulses and the excitation light at a time when the generation/detection unit 101 detects the electromagnetic wave pulses; a waveform obtaining unit 105 configured to obtain a time waveform of electromagnetic wave pulses from a first reflection portion and a second reflection portion of an object to be measured; a collecting position adjusting unit 106 configured to adjust a position where the electromagnetic wave pulses are collected with respect to the object to be measured; a measurement position information obtaining unit 107 configured to refer to outputs from the waveform obtaining unit 105 and the collecting position adjusting unit 106, and calculate positions of the reflection portions of the object to be measured; and a physical property obtaining unit 108 configured to refer to outputs from the waveform obtaining unit 105, the collecting position adjusting unit 106, and the measurement position information obtaining unit 107, and obtain physical properties such as a thickness and a refractive index of the object to be measured. An amount of movement of a collimated region in a portion where the electromagnetic wave pulses are collected is assumed equivalent to an amount of movement of the collecting position herein for description. In this embodiment, terahertz waves are used as the electromagnetic wave pulses for description, but a wavelength of the electromagnetic wave pulses in the present invention is not limited to a wavelength of a terahertz wave region.

The generation/detection unit 101 generates and detects terahertz wave pulses. The generation/detection unit 101 converts a change of electric field strength of the terahertz waves into a change of a current output from an element for detection. For example, a current corresponding to electric field strength of terahertz waves is detected by a change of photoconductivity in application of an excitation light. When the current is thus detected, an element (also herein referred to as a photoconductive element) having an antenna pattern formed of a metal electrode on a semiconductor film is applicable. Otherwise, an electric field can be detected using an electro-optic effect or a magnetic field can be detected using a magneto-optic effect herein. When an electric field is detected using an electro-optic effect, a polarization splitter and an electro-optic crystal may be used. When a magneto-optic effect is used to detect a magnetic field, a polarization splitter and a magneto-optic crystal may be used.

In the generation/detection unit 101 in FIG. 1, a portion configured to generate the terahertz waves may be shared with or separated from a portion for detection. When the portions are shared, the generation/detection unit 101 can generate and detect the terahertz waves with the same element configuration. In this case, an irradiation of an excitation light to a surface of a semiconductor or a nonlinear crystal may be applied to generate terahertz waves using an instantaneous current. A photoconductive element may be used to apply an electric field to an electrode of the photoconductive element when applying an excitation light to generate terahertz waves. An electro-optic effect of a nonlinear crystal may be used to generate terahertz waves by polarization generated by application of an excitation light. When the portions for generation and detection are separated, a configuration different from that of the portion for detection may be applied to the portion for generation. For example, in the case of using an instantaneous current, a PIN diode structure may be applied. Otherwise, interband transition of a carrier in a semiconductor quantum well structure may be used.

Figure 6A:
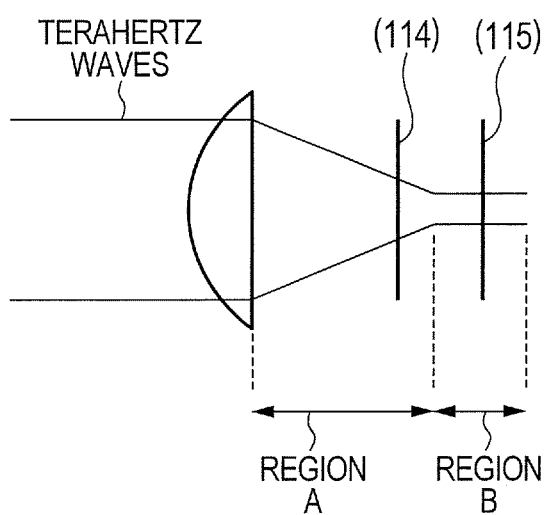
FIGS. 6A and 6B illustrate a beam shape and a positional relationship between reflection portions of an object to be measured.
Figure 6B:
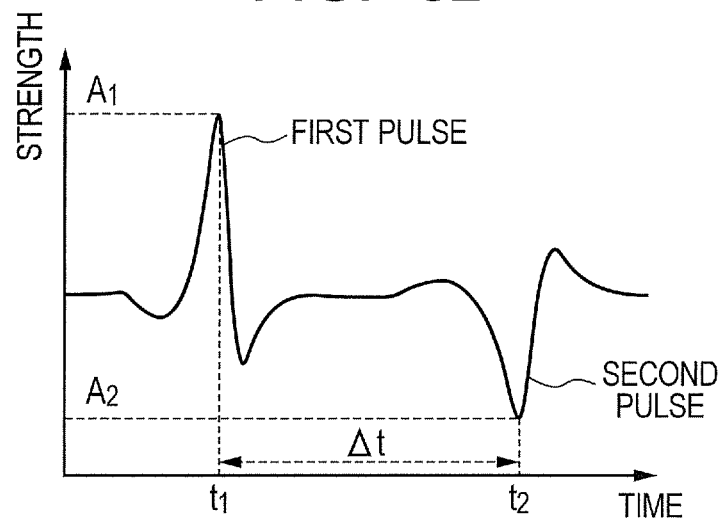

An example in which a photoconductive element is used as the generation/detection unit 101 is mainly described herein. The shaping unit 102 adjusts a beam shape of terahertz wave pulses. In FIG. 1, the shaping unit 102 is constituted by a casing with a window enclosing two lenses and the generation/detection unit 101. The shaping unit 102 collects the terahertz wave pulses using the two lenses 109 and 110. The shaping unit 102 may include an actuator 111 configured to move the lens on a window side in a propagation direction of the terahertz wave pulses. By adjusting a position of the lens 110 on the window side, a collecting position can be adjusted. When the shaping unit 102 encloses the generation/detection unit 101, the shaping unit 102 itself may have a mechanism moving in the propagation direction of the terahertz wave pulses so that a position where the terahertz wave pulses are collected is adjusted in the propagation direction of the terahertz wave pulses. Since the shaping unit 102 may only require having a function of collecting the terahertz wave pulses, it may include a mirror in place of the lens. As shown in FIGS. 6A and 6B, the beam shape of the terahertz wave pulses collected by the shaping unit 102 can wave-optically be classified roughly into a region in a process of the terahertz wave pulses being collected (region A, also referred to as a light collecting process region) and a region where the terahertz wave pulses propagate in a collimated shape (region B, also referred to as a collimated region).

The light source 103 supplies an excitation light to a photoconductive element that constitutes the generation/detection unit 101. In many cases, the light source 103 outputs an ultrashort pulse laser. The pulse laser output from the light source 103 has a pulse width of several tens of femtoseconds. The photoconductive element that constitutes the generation/detection unit 101 operates by exciting a carrier on a semiconductor thin film by application of an excitation light. As shown in FIG. 1, the excitation light output from the light source 103 is split into optical paths $L_1$ and $L_2$ by a beam splitter 112. An excitation light passing through the optical path $L_1$ is applied to the generation/detection unit 101 and used for generation. An excitation light passing through the optical path $L_2$ is applied to the generation/detection unit 101 via a delay optical unit 104 described later and used for detection. A wavelength of the excitation light emitted from the light source 103 changes depending on absorption wavelength of a semiconductor film of a photoconductive element used. In FIG. 1, although the generation unit and the detection unit of the terahertz waves are configured to be a common element, they may be separately configured as described above. Depending on absorption wavelength of the generation unit and the detection unit, a wavelength conversion element may be provided in a middle of the optical path $L_1$ or $L_2$. A wavelength, a pulse width of the light source 103, or a repetition frequency of the laser are selected according to required apparatus specifications. In FIG. 1, the common photoconductive element is used for generating and detecting the terahertz waves, and thus the excitation lights passing through the optical paths $L_1$ and $L_2$ are again combined into the same optical path by the beam splitter immediately before the generation/detection unit 101, collected by the lens 113 and guided to the shaping unit 102.

The delay optical unit 104 that is a delay portion adjusts optical path lengths of the excitation lights, and adjusts an optical path length difference between the excitation lights $L_1$ and $L_2$ reaching the generation/detection unit 101. Since, as described above, it is difficult to detect the terahertz waves in an actual time, the optical path length difference between the excitation lights $L_1$ and $L_2$ incident on the generation/detection unit 101 is successively changed by a predetermined amount to perform sampling measurement of the terahertz waves. The delay optical unit 104 may directly adjust the optical path length of the excitation light, or adjust an effective optical path length. When the optical path length is directly adjusted, a folded optical system configured to fold the excitation light and a movable portion configured to move the optical system in a folded direction may be used. At this time, a rotating system may be used as the movable portion so that the folded optical system moves in a rotational direction of the movable portion. As the light source 103, two laser sources configured to output the excitation lights $L_1$ and $L_2$ may be used to change the repetition frequency of each laser. In this case, a time difference between the two excitation lights reaching the generation/detection unit 101 relatively changes, and thus the time difference can be converted into an optical path length difference. When an effective optical path length is adjusted, a time constant in an optical path through which the excitation lights propagate can be changed. However, the configuration of the delay optical unit 104 is not limited to this, and any method may be used for achieving an object of adjusting an optical path length difference or a time difference that can be converted into the optical path length difference. FIG. 1 illustrates an example of using the folded optical system.

The waveform obtaining unit 105 refers to an output from the generation/detection unit 101 and constructs a time waveform of the terahertz waves. The terahertz waves typically have a pulse waveform of picosecond or less, and it is difficult to obtain the time waveform in an actual time. Thus, sampling measurement is performed with a pulsed light having a smaller pulse width than a pulse width of the terahertz wave. When the photoconductive element is used as the portion for detection, a pulsed light used for sampling is the above described excitation light. The excitation light is a pulsed light having a femtosecond pulse width. The sampling measurement of the terahertz waves is performed by adjusting an optical path length difference between the terahertz waves reaching the generation/detection unit 101 and the excitation light $L_2$ reaching the generation/detection unit 101. The optical path length difference is adjusted by the above described delay optical unit 104. The waveform obtaining unit 105 monitors an amount of adjustment of the optical path length difference by the delay optical unit 104 for the terahertz waves reaching the generation/detection unit 101, and plots an output from the generation/detection unit 101 depending on the amount of adjustment to construct a time waveform of the terahertz waves.

The collecting position adjusting unit 106 wave-optically refers to a portion which moves the collimated region of the terahertz wave pulses substantially along an optical axis of the terahertz wave pulses. For example, when the object to be measured has a first reflection portion 114 and a second reflection portion 115 in FIG. 1, the collecting position adjusting unit 106 moves the collecting position of the terahertz wave pulses from a position $P_1$ on the first reflection portion 114 to a position $P_2$ on the second reflection portion 115. In FIG. 1, the positions $P_1$ and $P_2$ are shown by points, but they actually are certain regions. Specifically, the collecting position adjusting unit 106 controls the actuator 111 provided in the shaping unit 102 to move the lens 110 on the side of the object to be measured substantially along the optical axis of the terahertz waves, and thus it adjusts the collecting position of the terahertz wave pulses. The collecting position adjusting unit 106 moves a position of the shaping unit 102 substantially along the optical axis of the terahertz waves to adjust the collecting position of the terahertz wave pulses. Also, the object to be measured is placed on the actuator 116, and the actuator 116 moves the position of the object to be measured substantially along the optical axis of the terahertz waves to relatively adjust the collecting position of the terahertz wave pulses.

The measurement position information obtaining unit 107 obtains a position of the first reflection portion 114 of the object to be measured from a change of the time waveform of the terahertz wave pulses with a change of the collecting position of the terahertz wave pulses. More specifically, the measurement position information obtaining unit 107 obtains a position where the collecting position $P_1$ of the terahertz wave pulses focused by the shaping unit 102 matches the first reflection portion 114 of the object to be measured. The collecting position of the terahertz wave pulses is adjusted by the collecting position adjusting unit 106. Concerning the time waveform of the terahertz wave pulses, the time waveform constructed by the waveform obtaining unit 105 is referred to. Specifically, shapes of a first pulse from the first reflection portion 114 of the object to be measured and a second pulse from the second reflection portion 115 are referred to. Although the first reflection portion 114 is located in a position closer to the generation/detection unit 101 than the second reflection portion 115 in FIG. 1, this placement relationship may be reversed. Another reflection portion may be provided between the first reflection portion 114 and the second reflection portion 115. As a result, information obtained by the measurement position information obtaining unit 107 is an amount of adjustment by the collecting position adjusting unit 106, and an amount of adjustment by the delay optical unit 104 required for detecting a pulse waveform (a part of the time waveform corresponding to the reflection portion) from a target reflection portion. These two amounts of adjustment are stored as measurement criteria.

The following description mainly concerns a method of obtaining an amount of adjustment by the collecting position adjusting unit 106. FIG. 6A illustrates a beam shape of the terahertz wave pulses in the collecting portion of the shaping unit 102 and a positional relationship between the first reflection portion 114 and the second reflection portion 115 of the object to be measured. FIG. 6B illustrates time waveforms of the first pulse and the second pulse of the terahertz wave pulses obtained from the reflection portions. As described above, the region in a process of the terahertz wave pulses being collected is referred to as the light collecting process region (region A), and the region where the terahertz wave pulses propagate in a collimated shape is referred to as the collimated region (region B). The collimated region wave-optically corresponds to a depth of focus. The collecting position by the shaping unit 102 is included in the collimated region. When a thickness of the object to be measured is t, and an average refractive index is n(ave), an optical length of the terahertz waves propagating through the object to be measured approximates to t×n. Meanwhile, an amount of movement of the collimated region in the object to be measured approximates to t/n(ave) in view of an angle of refraction of the terahertz waves with respect to the object to be measured. The amount of movement of the collimated region is equivalent to the amount of movement of the collecting position herein for description. The physical property obtaining unit 108 described later calculates the optical length and the amount of movement of the collimated region from the optical path length difference by the delay optical unit 104 and the amount of adjustment by the collecting position adjusting unit 106, and uniquely calculates the thickness t and the average refractive index n(ave) of the object to be measured.

When the reflection portion moves in the collimated region (region B), the beam shape of the terahertz waves reaching the generation/detection unit 101 does not change so much because wave-optically the terahertz waves are focused. Thus, an optical moving distance of the reflection portion with movement of the reflection portion in the collimated region (region B) is substantially proportional to a moving distance of the reflection portion. When the reflection portion moves in the light collecting process region (region A), the beam shape of the terahertz waves reaching the generation/detection unit 101 is scaled up and down with the movement of the reflection portion because wave-optically the terahertz waves are unfocused. More specifically, a propagation length of the terahertz waves reaching the generation/detection unit 101 is a value including the moving distance of the reflection portion and an angle component with scaling up and down of a beam diameter. Thus, the optical moving distance of the reflection portion with the movement of the reflection portion is longer than the optical moving distance in the collimated region (region B).

The optical moving distance can be converted into a propagation time of the terahertz wave pulses. Based on the above described phenomenon, the physical property obtaining apparatus with the terahertz wave pulses detects the pulses from the first reflection portion 114 and the second reflection portion 115 of the object to be measured, in which a time interval between the first pulse and the second pulse and strength thereof change depending on the region where each reflection portion is located. Specifically, three aspects described below are conceivable. A peak value of the pulse from the reflection portion is sometimes used as a value representing strength of the terahertz wave pulses.

In a first aspect, the first reflection portion 114 and the second reflection portion 115 are located within the light collecting process region (region A), and within this region, the positions of the reflection portions relatively move with the movement of the collecting position of the terahertz wave pulses. At this time, a time interval Δt in FIG. 6B does not change so much. Specifically, the time interval Δt changes by about a difference of the angle component with scaling up and down of the beam diameter of the terahertz wave pulses reaching the generation/detection unit 101, which change being mere as compared to the movement of the reflection portion. A ratio of a peak value $A_1$ of the first pulse from the first reflection portion 114 to a peak value $A_2$ of the second pulse from the second reflection portion 115 changes depending on loss or dispersion due to the physical properties or the structure of the object to be measured and also due to the collecting position. This is because a reflection signal from around the collimated region of the optical system in the shaping unit 102 is focused on the generation/detection unit 101, while a reflection signal from a position away from the focus of the optical system is incident in an unfocused manner on the generation/detection unit 101. More specifically, when the photoconductive element is used as the generation/detection unit 101, the antenna pattern on the photoconductive element spatially changes detection sensitivity in the element. Space distribution of the sensitivity can be regarded as a space filter. Thus, depending on the positional relationship between the light collecting process region of the optical system and the reflection portions, an amount of light per unit area of the terahertz wave pulses incident on the generation/detection unit 101 changes for the pulse signals from the reflection portions. A ratio of strength of the pulses from the reflection portions changes depending on the positional relationship. The photoconductive element is used as an example of the generation/detection unit 101, but not limited to this. Even if the detection element does not have a function of a space filter, the same operation can be performed by combining structural space filters such as minute apertures.

In a second aspect, the first reflection portion 114 and the second reflection portion 115 are located within the collimated region (region B), and within this region, the positions of the reflection portions relatively move with the movement of the collecting position of the terahertz wave pulses. At this time, the time interval Δt in FIG. 6B does not change so much because the optical moving distance of each reflection portion is substantially proportional to the physical moving distance as described above. Also, since the terahertz wave pulses propagate through the object to be measured as collimated beams, a strength ratio between the first pulse and the second pulse mainly depends on loss or dispersion due to the physical properties or the structure of the object to be measured.

In a third aspect, as shown in FIG. 6A, the first reflection portion 114 and the second reflection portion 115 range the light collecting process region (region A) and the collimated region (region B), and to satisfy this condition, the positions of the reflection portions relatively move with the movement of the collecting position of the terahertz wave pulses. This state is herein also referred to as a mixed region (region A+B). At this time, since propagation distances of the terahertz wave pulses are different by the angle component between the regions, the time interval Δt in FIG. 6B changes depending on the positions of the first reflection portion 114 and the second reflection portion 115. As described in the first aspect, the peak value $A_1$ of the first pulse from the first reflection portion 114 changes depending on the position of the first reflection portion 114 in the region A. Thus, the strength ratio of the peak value $A_1$ of the first pulse from the first reflection portion 114 to the peak value $A_2$ of the second pulse from the second reflection portion 115 changes depending on the collecting position of the terahertz wave pulses.

It is conventionally known that the depth of focus approximates to $n(\lambda)\lambda/2(NA)^2$. From this relationship, the depth of focus is estimated to be several mm for the terahertz waves. Here, $\lambda$ is a wavelength, $n(\lambda)$ is a refractive index (also herein referred to as refractive index dispersion) of each wavelength, and NA is the number of apertures of the optical system. As described above, when the depth of focus is sufficiently small for the object to be measured, the optical system of the shaping unit 102 functions as the confocal optical system. Thus, for example, the peak value of the first pulse can be monitored to specify the position of the first reflection portion 114. However, when the depth of focus is equivalent to the thickness of the object to be measured, the size of the collimated region (region B) through which the terahertz wave pulses propagate in a collimated shape cannot be ignored, which makes it difficult to specify the reflection portion. Specifically, when the depth of focus is equivalent to the thickness of the object to be measured, specification of the first reflection portion 114 by monitoring the peak value of the first pulse includes a measurement error of about the value of the depth of focus. The depth of focus being sufficiently small for the object to be measured refers to a size such that the terahertz wave pulses cannot be recognized as a structure. Specifically, this refers to an effective size of about ½₀ λ to ½₀₀ λ of a wavelength λ used, or an effective size corresponding to a half width of the terahertz wave pulses. The effective size includes refractive indexes of the object to be measured and an environment around the object to be measured. Typically, the size is several μm to several tens of μm.

Figure 7A:
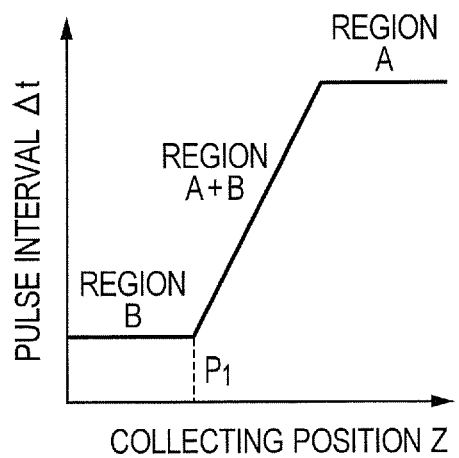
FIGS. 7A, 7B and 7C illustrate an operation of a measurement position information obtaining unit.
Figure 7B:
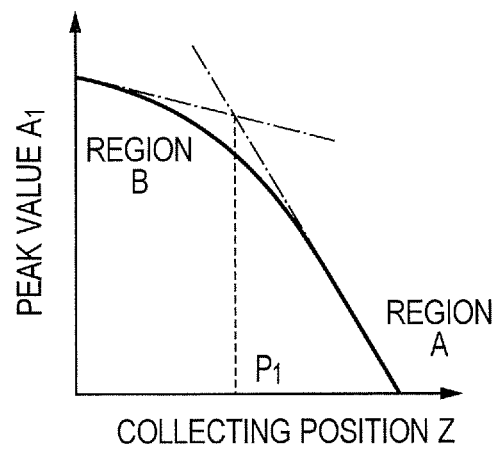
Figure 7C:
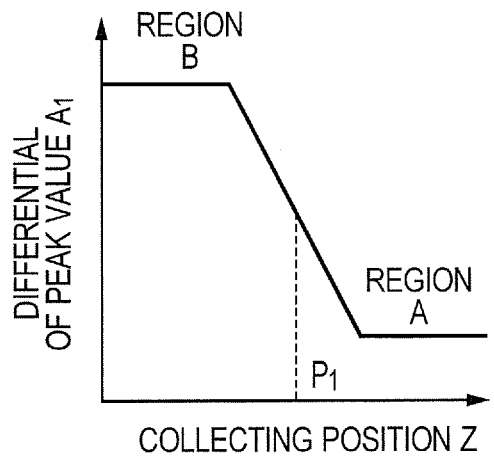

The measurement position information obtaining unit 107 uses the first pulse and the second pulse from the object to be measured to increase measurement accuracy for the position of the first reflection portion 114. In FIGS. 7A, 7B and 7C showing a specific method, a collecting position Z is an amount of adjustment by the collecting position adjusting unit 106. More specifically, the collecting position Z refers to a relative amount of movement with respect to a geometric optical focus. Thus, wave-optically, the collecting position Z is equivalent to the relative amount of movement of the collecting position. When the collecting position Z increases, the collecting position $P_1$ of the terahertz wave pulses moves inward of the object to be measured (direction from $P_1$ toward $P_2$ in FIG. 1).

FIG. 7A plots the interval Δt between the first pulse and the second pulse with the change of the collecting position Z. When the amount of adjustment of the collecting position Z is increased, the first reflection portion 114 and the second reflection portion 115 of the object to be measured move from the collimated region (region B) to the light collecting process region (region A). When each of the reflection portions are located in the collimated region (region B) or the light collecting process region (region A), the amount of change of the pulse interval Δt is smaller than the amount of adjustment of the collecting position Z as described above. However, when the reflection portions are located in the mixed region (region A+B), the terahertz wave pulses from the reflection portions to the generation/detection unit 101 have different relative propagation lengths, and thus the pulse interval Δt tends to increase with respect to the amount of adjustment of the collecting position Z. Specifically, in FIG. 6A, when the first reflection portion 114 is located in the light collecting process region (region A) and the second reflection portion 115 is located in the collimated region (region B), this phenomenon occurs. The amount of adjustment of the collecting position Z with a tendency of increase in the pulse interval Δt can be calculated to obtain a position where the collecting position $P_1$ of the terahertz wave pulses matches the first reflection portion of the object to be measured. More specifically, a position is obtained where the light collecting process region, the interface of the collimated region, and the first reflection portion of the object to be measured match. In FIG. 7A, the collecting position Z is moved from the mixed region (region A+B) to the light collecting process region (region A), and the amount of adjustment of the collecting position Z with a tendency of saturation of the pulse interval Δt can be calculated to obtain a position where the collecting position $P_2$ of the terahertz wave pulses matches the second reflection portion 115 of the object to be measured. More specifically, a position is obtained where the light collecting process region, the interface of the collimated region, and the second reflection portion 115 of the object to be measured match.

As the change of the time waveform, the change of the time interval between the first pulse and the second pulse with the movement of the collecting position of the terahertz wave pulses is used herein. Change information of the time interval can be used to specify the reflection portions of the object to be measured even under the condition that the light collecting process region and the collimated region of the beams of the terahertz wave pulses are mixed. This can increase measurement accuracy of the thickness t and the average refractive index n(ave) of the object to be measured.

FIG. 7B plots the peak value $A_1$ of the first pulse from the object to be measured with the change of the collecting position Z. When the first reflection portion 114 is located in the collimated region (region B), the terahertz wave pulses propagate through the object to be measured as collimated beams, and thus a rate of change of the peak value $A_1$ is low. This is because strength per unit area of the terahertz wave pulses focused on the generation/detection unit 101 does not change so much even if the position of the first reflection portion 114 changes in the collimated region (region B). However, when the first reflection portion 114 is located in the light collecting process region (region A), the strength per unit area of the terahertz wave pulses focused on the generation/detection unit 101 changes depending on the position of the first reflection portion 114, thereby increasing the rate of change. In other words, gradients of the peak value $A_1$ of the terahertz wave pulses with respect to the collecting position Z are different between the regions. A point of change of the gradient can be calculated to obtain a position where the collecting position $P_1$ of the terahertz wave pulses matches the first reflection portion 114 of the object to be measured. In FIG. 7B, to calculate the point of change of the gradient, asymptotes are calculated for the collimated region (region B) and the light collecting process region (region A), and a position where the asymptotes cross is determined as a position where the first reflection portion 114 of the object to be measured matches the collecting position $P_1$ of the terahertz wave pulses. More specifically, a position is obtained where the light collecting process region, the interface of the collimated region, and the first reflection portion 114 of the object to be measured match. The peak value $A_2$ of the second pulse from the object to be measured with the change of the collecting position Z can be plotted to obtain a position where the collecting position $P_2$ of the terahertz wave pulses matches the second reflection portion 115 of the object to be measured. More specifically, a position is obtained where the light collecting process region, the interface of the collimated region, and the second reflection portion 115 of the object to be measured match.

FIG. 7C shows a variant of FIG. 7B, where, to calculate the gradient of the peak value, a differential value of the peak value $A_1$ rather than the asymptote of the peak value is used. At this time, in the collimated region (region B) and the light collecting process region (region A), points of change of the differential value are calculated, and a midpoint of a connection thereof is calculated. The midpoint is determined as a position where the collecting position $P_1$ of the terahertz wave pulses matches the first reflection portion 114 of the object to be measured. More specifically, a position is obtained where the light collecting process region, the interface of the collimated region, and the first reflection portion 114 of the object to be measured match. The same processing can be performed for the second reflection portion 115 of the object to be measured to obtain a position where the collecting position $P_2$ of the terahertz wave pulses matches the second reflection portion 115 of the object to be measured. More specifically, a position is obtained where the light collecting process region, the interface of the collimated region, and the second reflection portion 115 of the object to be measured match.

The change of the time waveform herein is a change of the peak values of the first pulse and the second pulse with the movement of the collecting position of the terahertz wave pulses. Change information of the peak values can be used to specify the reflection portion of the object to be measured even under the condition that the light collecting process region and the collimated region of the beams of the terahertz wave pulses are mixed. This can increase measurement accuracy of the thickness t and the average refractive index n(ave) of the object to be measured. Such methods are selected depending on the property of the object to be measured or the configuration of the apparatus.

Figure 17:
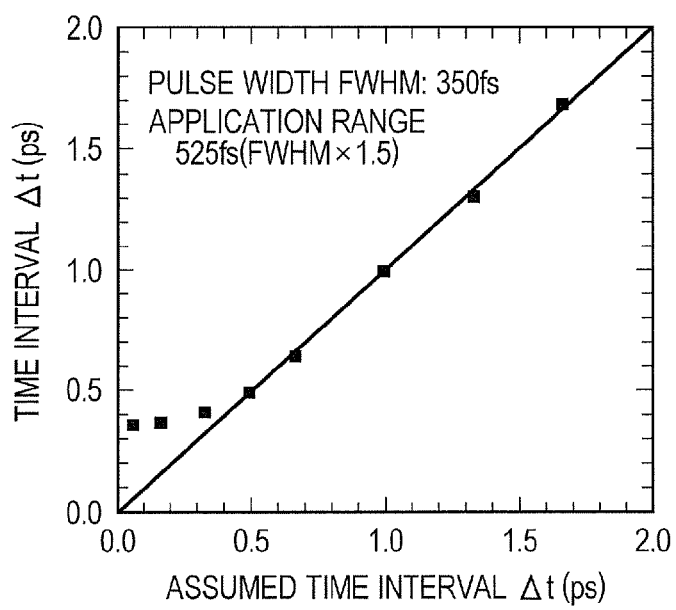
FIG. 17 illustrates processing accuracy of the measurement position information obtaining unit.

In FIG. 6B, when the first pulse and the second pulse are close to each other, the pulses may be superimposed to change the time waveform. In this case, it is assumed that the time interval Δt or the peak values $A_1$ and $A_2$ has an error, which may reduce processing accuracy of the measurement position information obtaining unit 107. For example, FIG. 17 plots an assumed time interval Δt converted from the thickness of the object to be measured and a time interval Δt actually measured. A half width (FWHM) of the terahertz wave pulses at this time is 350 femtoseconds. Ideally, the ordinate and the abscissa in FIG. 17 should indicate the same value, but actually, when the first pulse and the second pulse are close to each other, the ordinate and the abscissa indicate different values. Specifically, if the pulses from the reflection portions are close to a time region of about 1.5 times (about 530 femtoseconds in FIG. 17) the half width of the terahertz wave pulses used, the assumed time interval may be deviated from the measured time interval.

Figure 8A:
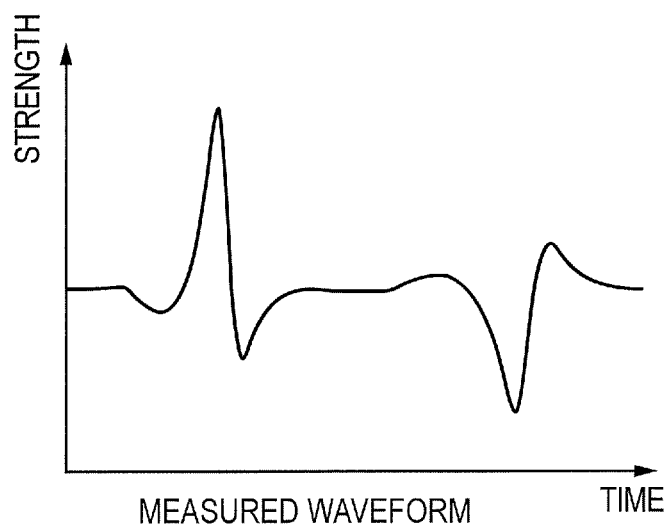
FIGS. 8A, 8B and 8C illustrate a method of increasing accuracy of the measurement position information obtaining unit.
Figure 8B:
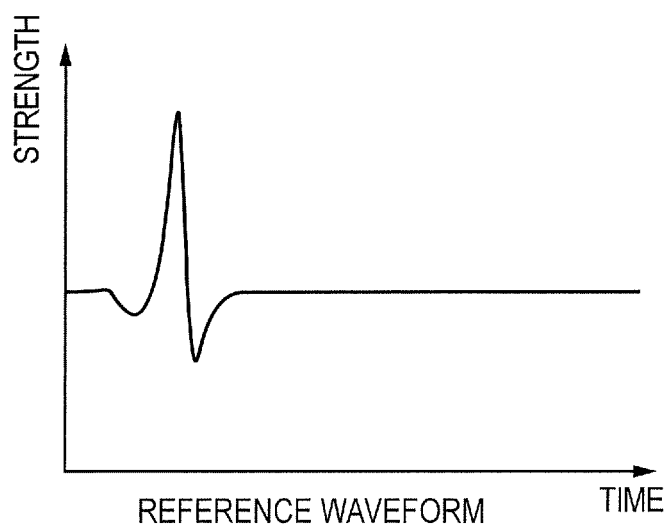
Figure 8C:
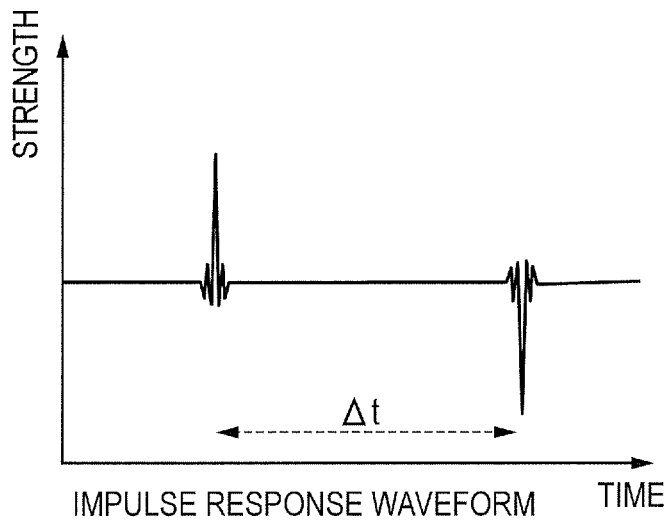

To maintain the processing accuracy of the measurement position information obtaining unit 107 even under such a condition, the measurement position information obtaining unit 107 desirably includes compensation processing as described below. For example, as shown in FIGS. 8A, 8B and 8C, as the compensation processing, a reference waveform of previously measured terahertz wave pulses is used to perform deconvolution of measured terahertz wave pulses to calculate an impulse response waveform from the object to be measured. As a reference waveform in FIG. 8B, for example, a complete reflection waveform of the terahertz wave pulses formed by metal or the like is used. When deconvolution of a measured waveform in FIG. 8A is performed with the reference waveform, an impulse response waveform in FIG. 8C can be obtained. Since the obtained impulse response waveform has a smaller half width than the first pulse and the second pulse shown in FIG. 6B, even with the first pulse and the second pulse being close to each other, processing accuracy of specification of the first reflection portion of the object to be measured can be maintained.

Figure 9A:
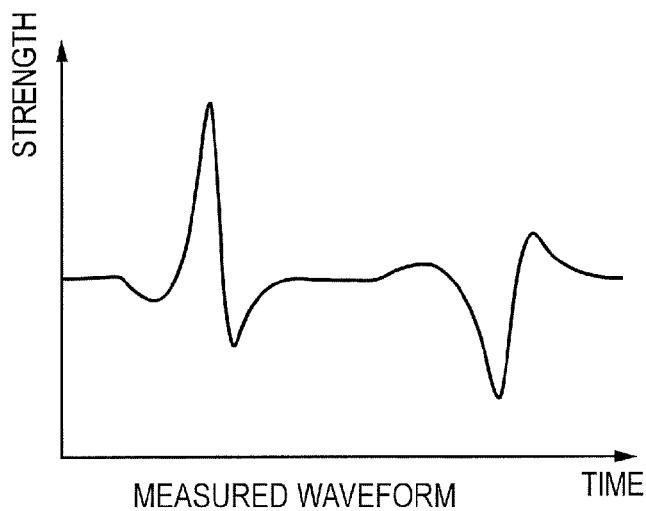
FIGS. 9A, 9B and 9C illustrate a method of increasing accuracy of the measurement position information obtaining unit.
Figure 9B:
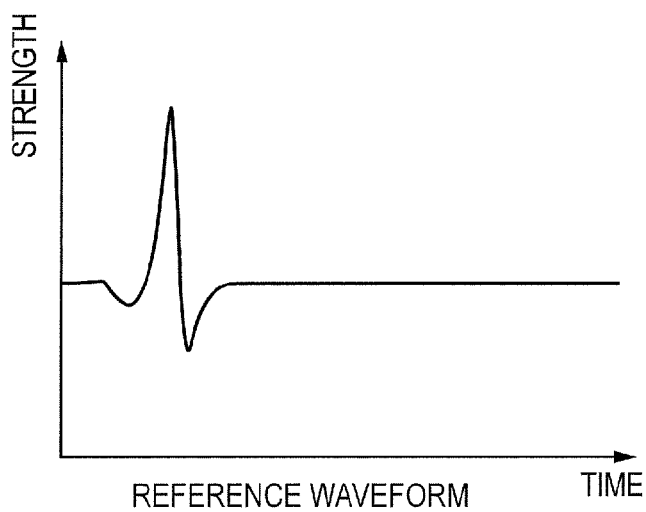
Figure 9C:
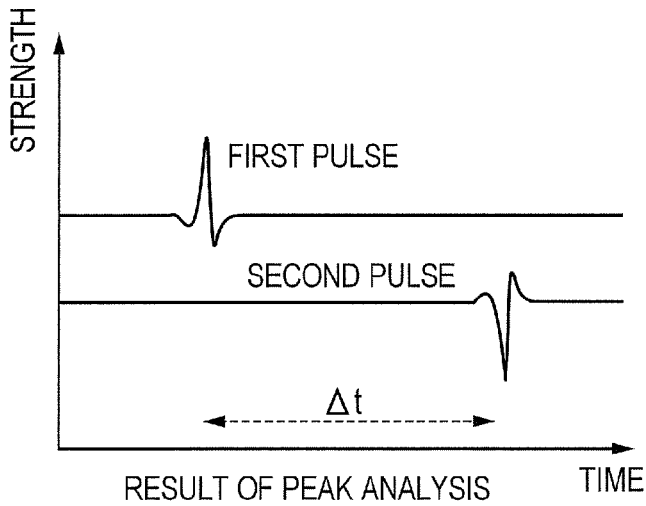

As shown in FIGS. 9A, 9B and 9C, a reference waveform may be used to perform peak analysis. It is assumed that a measured waveform in FIG. 9A can be reconstructed by a combination of a plurality of reference waveforms in FIG. 9B, and a position, strength and a phase of each reference waveform are adjusted by regression analysis so as to minimize an error between the reconstructed waveform and the measured waveform. In other words, the first pulse and the second pulse are separated from the measured waveform using the reference waveform. For example, in FIG. 9C, it is assumed that the measured waveform can be reconstructed by a combination of two reference waveforms, and peak analysis is performed. From a result of the peak analysis in FIG. 9C, two reference waveforms with adjusted position, strength and phase on a time axis can be obtained as the first pulse and the second pulse. From the adjusted two reference waveforms, the time interval Δt and the peak values $A_1$ and $A_2$ are obtained to obtain the reflection portion of the above described object to be measured. As such, the peak analysis by regression analysis is performed as the compensation processing, and thus processing accuracy of specification of the first reflection portion of the object to be measured can be maintained even if the first pulse and the second pulse are close to each other.

With such a combination of processing, the measurement position information obtaining unit 107 monitors the changes of the time waveforms of the first pulse and the second pulse reflected from the first reflection portion 114 and the second reflection portion 115 with the change of the collecting position of the terahertz wave pulses. An amount of adjustment $Z_1$ by the collecting position adjusting unit 106 when the collimated region of the terahertz wave pulses matches the first reflection portion 114 and an optical path length difference $D_1$ by the delay optical unit 104 required for detecting the first pulse are obtained as measurement references. More specifically, the optical path length difference $D_1$ is an amount of adjustment by the delay optical unit 104 required for the generation/detection unit 101 to detect a peak portion of the first pulse at the amount of adjustment $Z_1$ by the collecting position adjusting unit 106. As described above, when the first pulse and the second pulse are close to each other, each amount of adjustment is obtained by referring to the time interval or strength obtained by the compensation processing.

The physical property obtaining unit 108 calculates the thickness t and the average refractive index n(ave) of the region between the first reflection portion 114 and the second reflection portion 115 of the object to be measured. More specifically, an amount of adjustment $Z_2$ by the collecting position adjusting unit 106 when the collimated region of the terahertz wave pulses matches the second reflection portion 115 and an optical path length difference $D_2$ by the delay optical unit 104 required for detecting the second pulse are obtained. From an amount of change $|Z_2-Z_1|$ by the collecting position adjusting unit 106 and an amount of change $|D_2-D_1|$ by the delay optical unit 104, the thickness t and the average refractive index n(ave) of the region between the first reflection portion 114 and the second reflection portion 115 are calculated.

A calculation method of the thickness t and the average refractive index n(ave) of the region between the first reflection portion 114 and the second reflection portion 115 is as follows. As the detailed deriving method described in PTL 2, when the object to be measured relatively moves substantially in the propagation direction of the terahertz wave pulses, the thickness t and the average refractive index n(ave) are calculated by Expressions (1) and (2) below. The expressions are obtained by writing expressions using an incident angle, an incident position, an angle of refraction, or the like of the pulses with respect to the object to be measured and straightening the expressions. Since the object to be measured relatively moves, Expression (1) includes a term of $|Z_2-Z_1|$.

$$|D_2 - D_1| = n \times t - |Z_2 - Z_1| \quad (1)$$

$$n^2 = \frac{1}{2}\left\{\sin^2\theta + \sqrt{\sin^4\theta + 4(1-\sin^2\theta)\times\left(1+\frac{|D_2-D_1|}{|Z_2-Z_1|}\right)^2}\right\} \quad (2)$$

Sin θ is the number of apertures (NA) in the atmosphere of the optical system in the shaping unit 102. When a distance between the generation/detection unit 101 and the object to be measured does not change but only the collecting position of the terahertz wave pulses changes, the thickness t and the refractive index n are calculated by Expressions (3) and (4) below. This aspect corresponds to, for example, a case of moving the position of the lens on the side of the object to be measured used for collecting the terahertz wave pulses in FIG. 1. Here, since the position of the lens is moved, Expression (3) does not include the term of $|Z_2-Z_1|$.

$$|D_2 - D_1| = n \times t \quad (3)$$

$$n^2 = \frac{1}{2}\left\{\sin^2\theta + \sqrt{\sin^4\theta + 4(1-\sin^2\theta)\times\left(\frac{|D_2-D_1|}{|Z_2-Z_1|}\right)^2}\right\} \quad (4)$$

The physical property obtaining unit 108 calculates the refractive index from a ratio of the change of the collecting position to the change of the optical path length difference when the collecting position of the terahertz wave pulses is changed from the measurement references. Then, the thickness is calculated.

As described above, the depth of focus (collimated region) of the optical system approximates to $n(\lambda)\lambda/2(NA)^2$, and thus an increase in the number of apertures reduces the size of the collimated region. If it is assumed that the terahertz wave pulses propagate as a Gaussian beam, θ approximates to $\lambda/\pi w_0$ (rad). Here, $w_0$ is a beam spot radius of the terahertz wave pulses. The beam spot radius of the terahertz wave pulses is reduced with increasing number of apertures. Thus, for a measurement range in a horizontal direction with respect to the object to be measured (also substantially in a horizontal direction with respect to an incident direction of the terahertz wave pulses), the number of apertures is desirably determined so as to set the beam spot radius to a value not exceeding a desired measurement range.

The increase in the number of apertures reduces the size of the collimated region, and thus the pulse interval, as shown in FIG. 7A, steeply changes for the amount of adjustment by the collecting position adjusting unit 106. This tends to cause a steep change of the pulse interval for a minimum adjustment ability of the collecting position adjusting unit 106. When the collecting position adjusting unit 106 does not have a sufficient minimum adjustment ability for the change of the pulse interval, detection accuracy of the reflection portion of the object to be measured is reduced. On the other hand, to increase the detection accuracy of the reflection portion, the size of the collimated region may be increased, and the amount of change of the pulse interval for a minimum amount of adjustment by the collecting position adjusting unit 106 may be reduced to observe the change of the pulse interval in detail. However, depending on the size of the collimated region, the change of the pulse interval may exceed an adjustment limit of the collecting position adjusting unit 106. Thus, the size of the collimated region is set so that the change of the pulse interval falls within the adjustment limit by the collecting position adjusting unit 106. The detection accuracy of the reflection portion has an influence on processing accuracy of the above described physical property obtaining unit 108. In short, the increase in the size of the collimated region tends to increase processing accuracy of the physical property obtaining unit 108. Thus, the number of apertures is desirably determined depending on measurement accuracy of the required thickness t and average refractive index n(ave) of the object to be measured. The number of apertures is desirably determined so as to satisfy demands of a required measurement range set by a beam spot radius and the processing accuracy of the physical property obtaining unit 108.

In addition, in the case of application to an apparatus configured to obtain an image from the time interval between the first pulse and the second pulse such as a tomographic image obtaining apparatus described later, at least a region of about an interval between the first reflection portion 114 and the second reflection portion 115 is desirably ensured as a depth of focus. This is because if the depth of focus is extremely smaller than the interval between the first reflection portion 114 and the second reflection portion 115, a change of the optical path length by an influence of the light collecting process region is superimposed on the time interval between the pulses from the reflection portions. In this case, the obtained tomographic image needs to be further subjected to processing for reducing the influence of the optical system. Thus, in the tomographic image obtaining apparatus, the number of apertures of the optical system is desirably selected so as to further satisfy a condition of the collimated region considering a required horizontal observation region and the interval between the first reflection portion 114 and the second reflection portion 115.

Figure 4:
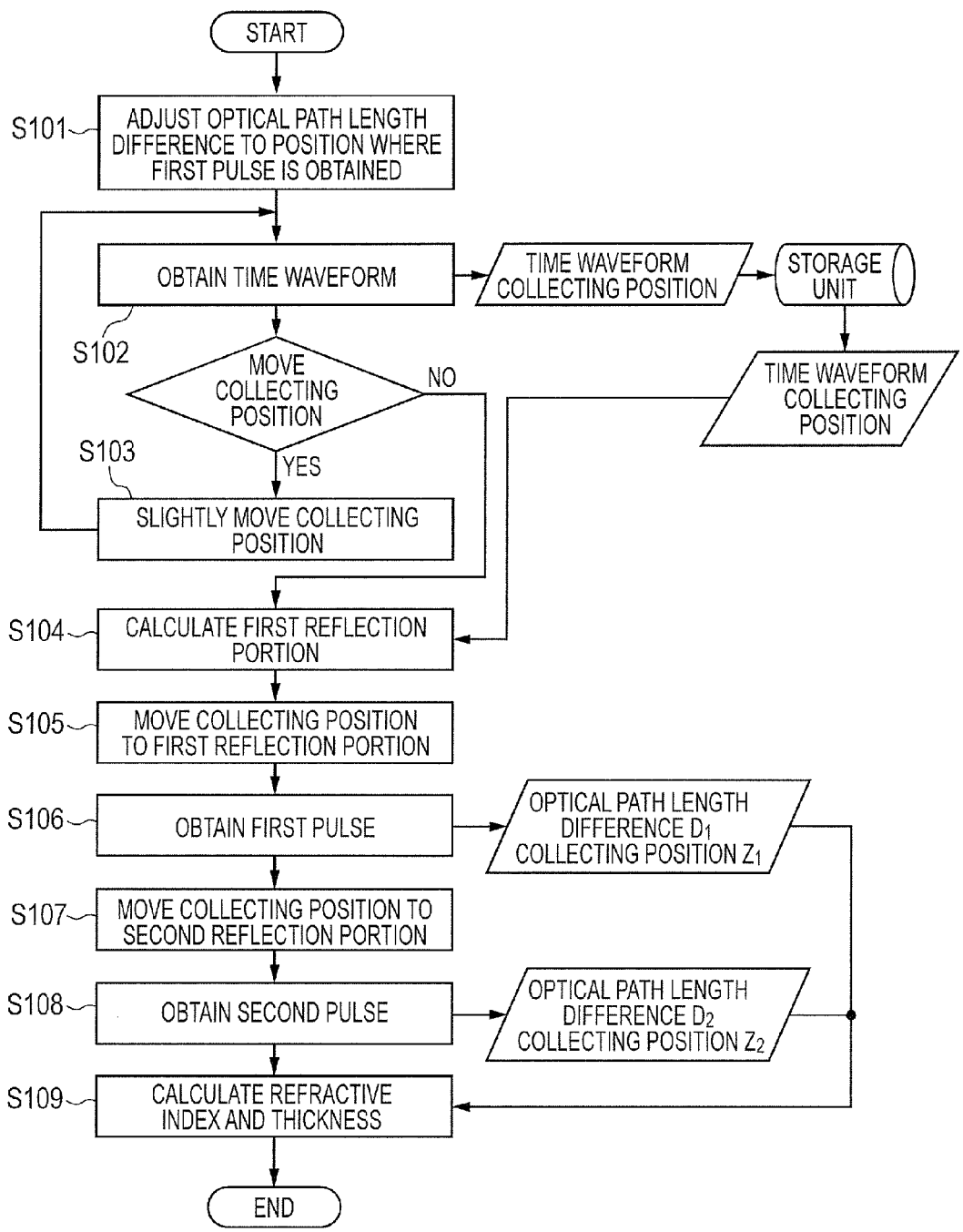
FIG. 4 illustrates an operation of the apparatus of Embodiment 1.

FIG. 4 is a typical operation flow of the apparatus of this embodiment. When the measurement is started, the apparatus uses the delay optical unit 104 to adjust the optical path length difference to a position where the first pulse from the first reflection portion of the object to be measured can be detected (S101). The optical path length difference may be a machine origin determined by the delay optical unit 104, or may be determined by measuring a placement state of the object to be measured using a camera or a distance measuring unit. A time waveform of the terahertz wave pulses may be measured once to determine the optical path length difference.

The waveform obtaining unit 105 obtains the time waveform of the terahertz wave pulses by time-domain spectroscopy, and stores information of the time waveform and the collecting position of the terahertz wave pulses in a storage unit of the apparatus (S102). The stored collecting position is equal to an amount of adjustment by the collecting position adjusting unit 106. The time waveform of the terahertz wave pulses includes at least the first pulse and the second pulse. It is determined whether the collecting position is to be moved. This determination is made, for example, by determining whether a fixed number of times of measurement is satisfied. Otherwise, the determination is made by determining whether a previously determined amount of movement of the collecting position is ensured. The determination is desirably made by determining whether the collecting position of the terahertz wave pulses is moved from the first reflection portion 114 to the second reflection portion 115 in a region including at least the first reflection portion 114 and the second reflection portion 115 of the object to be measured.

When the collecting position is moved, the collecting position adjusting unit 106 is used to slightly move the collecting position of the terahertz wave pulses (S103). Then, the time waveform of the terahertz wave pulses is again obtained by the waveform obtaining unit 105, and the information of the time waveform and the collecting position of the terahertz wave pulses (the amount of adjustment by the collecting position adjusting unit 106) are stored in the storage unit of the apparatus (S102). After the measurement of the time waveform of the terahertz wave pulses with movement of the collecting position of the terahertz wave pulses is finished, the apparatus uses the measurement position information obtaining unit 107 to calculate the first reflection portion 114 of the object to be measured (S104). Specifically, from the change of the time waveform of the terahertz wave pulses for the amount of adjustment by the collecting position adjusting unit 106 as shown in FIGS. 7A, 7B and 7C, a position is specified where the first reflection portion 114 matches the collecting position $P_1$ of the terahertz wave pulses.

After the first reflection portion 114 is calculated, the apparatus uses the collecting position adjusting unit 106 to move the collecting position of the terahertz wave pulses to the first reflection portion 114 (S105). When the storage unit has already obtained the time waveform of the terahertz wave pulses for the desired amount of adjustment by the collecting position adjusting unit 106, the amount of adjustment by the collecting position adjusting unit 106 required for the movement to the first reflection portion 114 may be invoked. After the movement of the collecting position is completed, the physical property obtaining unit 108 obtains the first pulse from the first reflection portion 114 (S106). The first pulse is obtained from a time waveform of the terahertz wave pulses measured by the waveform obtaining unit 105. The time waveform stored in the storage unit may be used to invoke the time waveform of the terahertz wave pulses corresponding to the desired collecting position and obtain the first pulse. The physical property obtaining unit 108 obtains the optical path length difference $D_1$ and the collecting position $Z_1$ corresponding to the first pulse.

The collecting position adjusting unit 106 moves the collecting position $P_2$ of the terahertz wave pulses to a position matching the second reflection portion 115 of the object to be measured (S107). The measurement position information obtaining unit 107 calculates the position of the second reflection portion 115 of the object to be measured by invoking information of the time waveform of the terahertz wave pulses for the amount of adjustment by the collecting position adjusting unit 106 stored in the storage unit.

The collecting position adjusting unit 106 may gradually moves the collecting position of the terahertz wave pulses from $P_1$ toward $P_2$, and the measurement position information obtaining unit 107 may monitor the position of the second reflection portion 115 in real time. Similar to S105, when the storage unit has already obtained the time waveform of the terahertz wave pulses for the desired amount of adjustment by the collecting position adjusting unit 106, the amount of adjustment by the collecting position adjusting unit 106 required for movement to the second reflection portion 115 may be invoked.

After the movement of the collecting position is completed, the physical property obtaining unit 108 obtains the second pulse from the second reflection portion 115 (S108). The second pulse is obtained from the time waveform of the terahertz wave pulses measured by the waveform obtaining unit 105. The time waveform stored in the storage unit may be used to invoke the time waveform of the terahertz wave pulses corresponding to a desired collecting position to obtain the second pulse. The physical property obtaining unit 108 obtains the optical path length difference $D_2$ and the collecting position $Z_2$ corresponding to the second pulse. The physical property obtaining unit 108 uses any one of Expressions (1) to (4) to calculate the thickness t and the average refractive index n(ave) of the region between the first reflection portion 114 and the second reflection portion 115 from the amount of change $|Z_2-Z_1|$ by the collecting position adjusting unit 106 and the amount of change $|D_2-D_1|$ by the delay optical unit 104 (S109).

From the configuration and the operation process as described above, the physical property measurement apparatus of this embodiment obtains the thickness t and the average refractive index n(ave) of the object to be measured. According to the apparatus configuration of this embodiment, the position of the reflection portion of the object to be measured is calculated by the changes of the time waveforms of the first pulse and the second pulse with the change of the collecting position of the terahertz wave pulses. As a result, even if the size of the region between the reflection portions of the object to be measured is close to the value of the depth of focus of the terahertz wave pulses, the position of each reflection portion can be accurately specified. This can provide an apparatus that can increase detection accuracy of the thickness t and the average refractive index n(ave) of the region between the first reflection portion and the second reflection portion.

For the same reason, detection accuracy is increased of the thickness t and the average refractive index n(ave) of the region between the first reflection portion 114 and the second reflection portion 115. The apparatus and method of this embodiment use the terahertz wave pulses. Thus, using transmission of the terahertz wave pulses allows specification of the physical properties of the inner structure at a depth of about several hundreds of µm to several tens of mm.

Embodiment 2

Another aspect for carrying out the idea of the present invention will be described with reference to the drawings. This embodiment is a variant of Embodiment 1. Specifically, this embodiment relates to an apparatus and a method configured to identify an object to be measured from a shape of terahertz wave pulses. Descriptions on the same components as those in the above description will be omitted.

Figure 2:
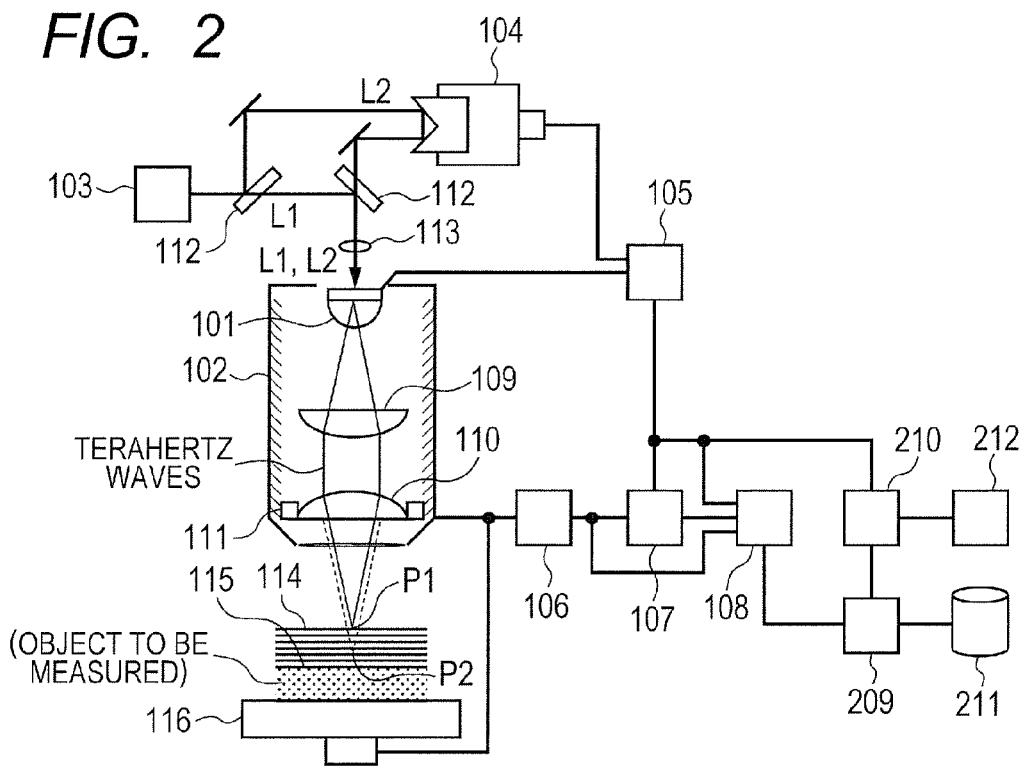
FIG. 2 is a schematic configuration diagram of an apparatus described in Embodiment 2.

FIG. 2 is a schematic configuration diagram of a physical property measurement apparatus of this embodiment. This apparatus includes a portion configured to identify the object to be measured in addition to the configuration of the apparatus described in Embodiment 1. The portion configured to identify the object to be measured includes at least: a database 211 that stores physical property information and a time waveform of terahertz wave pulses for each material; a waveform adjusting unit 209 configured to select, from the database 211, a candidate material for a region between a first reflection portion 114 and a second reflection portion 115 by an average refractive index n(ave) obtained by the apparatus, and adjust a time waveform of the candidate material to a time waveform including an influence of a thickness t and the stored physical property; a waveform comparing unit 210 configured to compare the measured time waveform of the terahertz wave pulses with the time waveform by the waveform adjusting unit 209; and a physical property specifying unit 212 configured to specify a material highly correlated with the measured waveform from an output from the waveform comparing unit 210.

The physical property information stored in the database 211 is frequency spectrum information of a terahertz wave region. The frequency spectrum information is information on an absorption spectrum or refractive index dispersion n(λ) of the material. The stored time waveform of the terahertz wave pulses is desirably the time waveform measured by the apparatus described in this embodiment. However, time waveforms measured by the same apparatus do not always need to be used. For example, time waveforms measured by the same apparatus configuration may be used. Time waveforms measured by other apparatus configurations may be used if an influence typical of the apparatus (accuracy or measurement band) is already known. In this case, a difference between the apparatuses is stored in the database 211 as a system function. A measurement condition (temperature, humidity, or atmosphere) when each material is measured is desirably stored in the database 211 as a system function. Outer shape information (thickness) of the material used for measurement is also stored in the database 211. The time waveform stored in the database 211 desirably includes a first pulse and a second pulse.

The average refractive index n(ave) of the object to be measured that is measured by the physical property obtaining unit 108 configured to adjust the time waveform of the material stored in the database 211 is referred to, and a material having a similar average refractive index n(ave) is screened from the database 211. The waveform adjusting unit 209 adjusts a time waveform of a candidate material obtained by screening. Specifically, the average refractive index n(ave) and the thickness t of the object to be measured that are measured by the physical property obtaining unit 108 is referred to, and when the outer shape (thickness) is different from that of the material stored in the database 211, an interval between the first pulse and the second pulse of the time waveform invoked from the database 211 is adjusted. When the interval between the first pulse and the second pulse is adjusted, physical property information (for example, refractive index dispersion $n(\lambda)$, an absorption coefficient, a frequency spectrum, or the like) of the candidate material stored in the database 211 is referred to, and dispersion typical of the material when a propagation distance of the terahertz wave pulses changes is desirably compensated. Specifically, the influence of dispersion typical of the material is compensated to adjust the shape of the time waveform of each pulse. To reduce the influence of a difference between the apparatuses or a difference in measurement condition, the system function of the candidate material stored in the database 211 may be referred to, and convolution of the adjusted time waveform may be performed.

The waveform comparing unit 210 compares the time waveform of the candidate material adjusted by the waveform adjusting unit 209 with the waveform measured by the waveform obtaining unit 105. Specifically, residuals of the time waveform by the waveform adjusting unit 209 and the time waveform by the waveform obtaining unit 105 are output. Alternatively, a correlation between the time waveform by the waveform adjusting unit 209 and the time waveform by the waveform obtaining unit 105 is checked. An area of comparison in the time waveform may be the entire time waveform obtained, or only a characteristic portion (for example, the first pulse or the second pulse). The physical property specifying unit 212 refers to the output from the waveform comparing unit 210 to select a candidate material closest to the object to be measured. Physical properties (for example, refractive index dispersion $n(\lambda)$, an absorption coefficient, a frequency spectrum, or the like) and a type of the object to be measured are presented to the operator of the apparatus.

Figure 5:
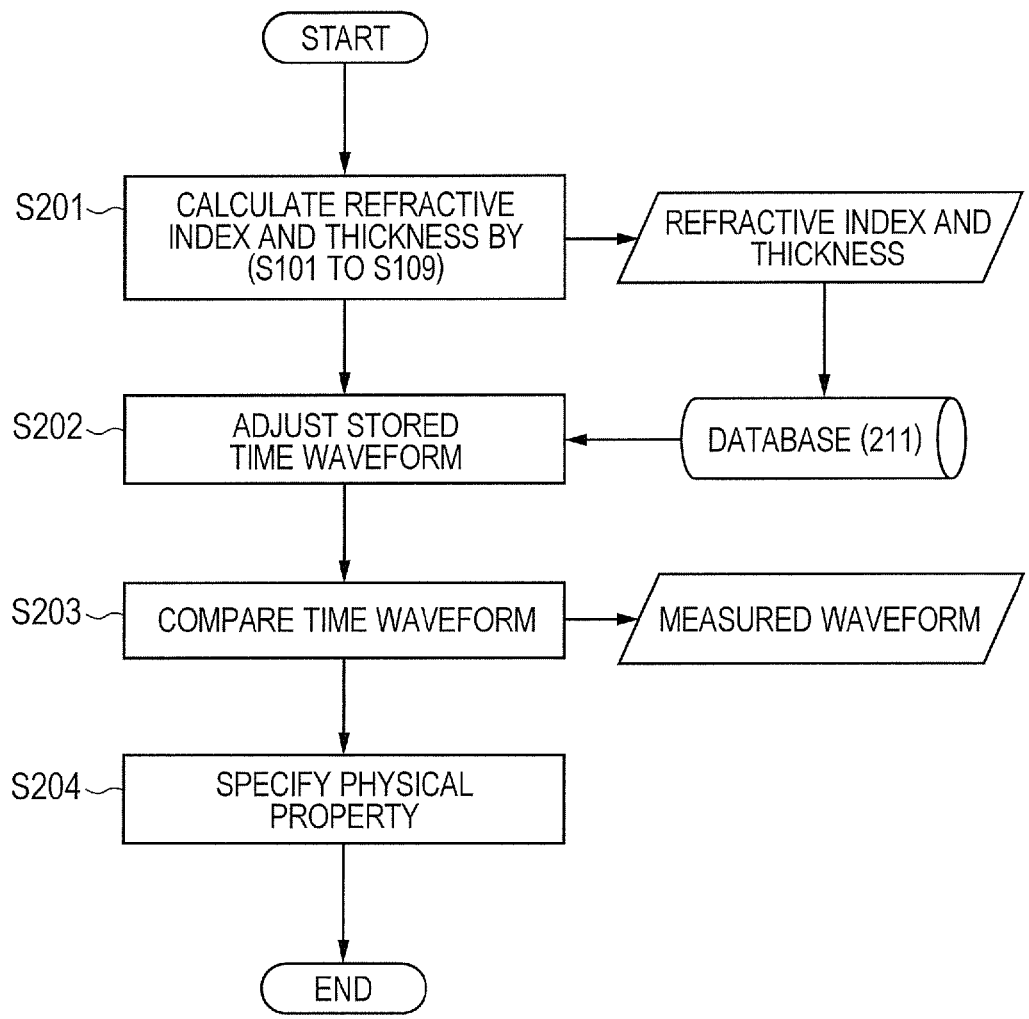
FIG. 5 illustrates an operation of the apparatus of Embodiment 2.

FIG. 5 is a typical operation flow relating to the apparatus of this embodiment. For the operation flow, descriptions on the same components as those in the above description will be omitted. The apparatus moves the collecting position of the terahertz wave pulses to a spot where a physical property is to be specified. The apparatus calculates the average refractive index n(ave) and the thickness t of the object to be measured by the steps S101 to S109 described in Embodiment 1 (S201). Such information is output from the physical property obtaining unit 108. To the waveform obtaining unit 105, the time waveform of the terahertz wave pulses relating to the object to be measured is output. In the database 211, a plurality of candidate materials of the object to be measured is selected from the materials stored in the database 211 by referring to the average refractive index n(ave) output from the physical property obtaining unit 108. The waveform adjusting unit 209 adjusts the time waveform linked to each candidate material (S202). The waveform comparing unit 210 compares the time waveform of the terahertz wave pulses output from the waveform adjusting unit 209 with the time waveform of the terahertz wave pulses output from the waveform obtaining unit 105 (S203).

The physical property specifying unit 212 refers to the output from the waveform comparing unit 210 to specify a candidate material closest to the object to be measured (S204). The physical property specifying unit 212 then presents the physical property and the type of the object to be measured to the operator. For example, refractive index dispersion $n(\lambda)$, an absorption coefficient, a frequency spectrum, or the like are presented as the physical properties. Although in Step S202, a plurality of candidate materials is selected to collectively adjust time waveforms, an action of selecting one material and then performing the steps S202 to S204 may otherwise be performed several times. In this case, the physical property specifying unit 212 desirably determines a condition for the object to be measured to match the candidate material. In the method of collectively selecting the candidate materials, a material close to the object to be measured is determined from the selected materials, thereby always concentrating a comparing operation. This increases stability of an apparatus operation. The method of successively selecting the candidate materials and checking matching reduces a load required for calculation for each processing, thereby reducing the need for large-scale calculation. Thus, power saving and a cost reduction of the apparatus can be expected.

According to the measurement apparatus of this embodiment, the time waveform of the terahertz wave pulses from the reflection portion of the object to be measured is compared with the time waveform of the material previously stored in the database to check the physical property of the object to be measured. This can provide an apparatus that allows specification of the material for the object to be measured. According to the measurement method of this embodiment, the material for the object to be measured can be specified for the same reason.

Embodiment 3

Another aspect for carrying out the idea of the present invention will be described with reference to the drawings. This embodiment is a variant of the above described embodiment. Specifically, this embodiment has a different configuration of a portion configured to generate and detect terahertz wave pulses. Descriptions on the same components as those in the above description will be omitted.

Figure 3A:
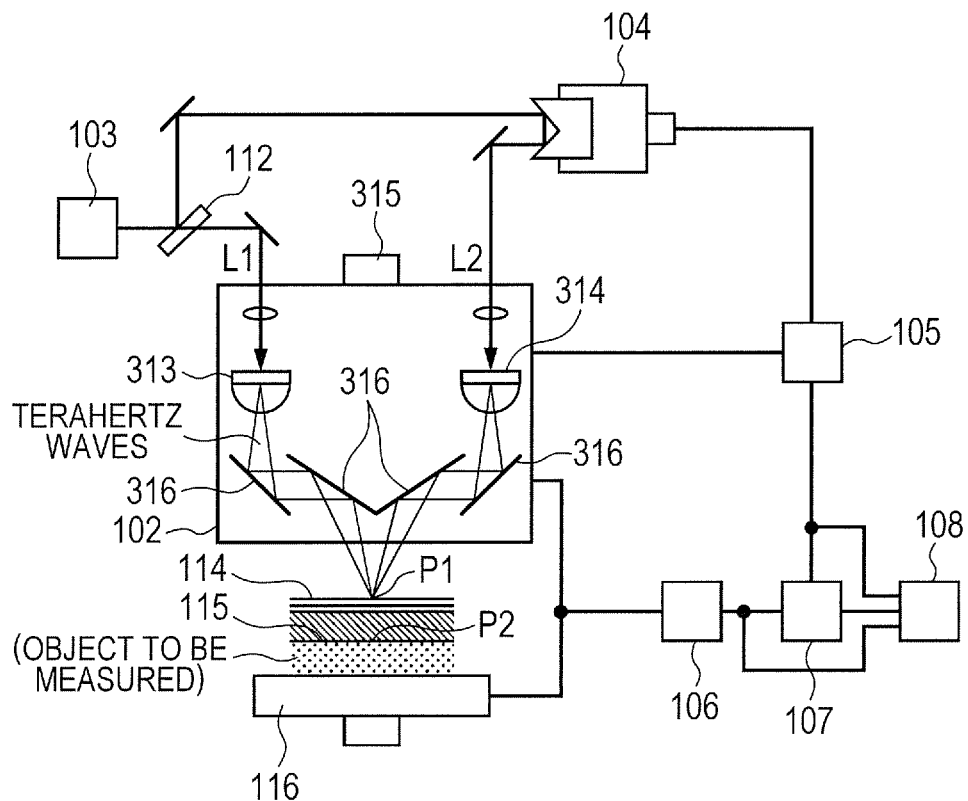
FIGS. 3A and 3B are schematic configuration diagrams of an apparatus described in Embodiment 3.
Figure 3B:
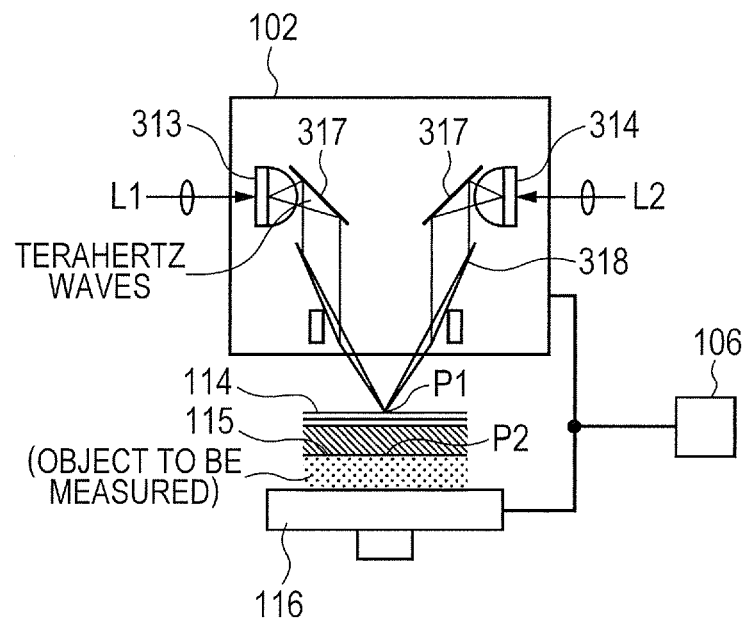

FIGS. 3A and 3B are schematic configuration diagrams of a physical property measurement apparatus of this embodiment. A variant of the measurement apparatus of Embodiment 1 is shown. A difference from Embodiment 1 is that two elements: a generation unit 313 and a detection unit 314, is used in place of the generation/detection unit 101. In the above described embodiments, the same photoconductive element is used for generation and detection, but this element is divided into two parts to increase flexibility in selection. For example, an element having a high output of terahertz wave pulses can be selected as the generation unit 313, and an element having high detection sensitivity can be used as the detection unit 314. Thus, increasing selectivity of the apparatus can easily address various demands for the apparatus.

A shaping unit 102 in FIG. 3A uses four mirrors 316 to collect terahertz wave pulses on an object to be measured, and at this time, an application direction of excitation lights $L_1$ and $L_2$ matches an application direction of the terahertz wave pulses. With such a configuration, when the shaping unit 102 includes the generation unit 313 and the detection unit 314, the shaping unit 102 can be moved in the application direction of the excitation lights to move a collecting position of the terahertz wave pulses. This movement is performed by an actuator 315 provided in the shaping unit 102. FIG. 3B shows a variant of the shaping unit 102, and the application direction of the excitation lights $L_1$ and $L_2$ is substantially perpendicular to the application direction of the terahertz wave pulses by two mirrors 317. In this case, the actuator can move two mirrors 318 on the side of the object to be measured in the application direction of the terahertz wave pulses to move the collecting position of the terahertz wave pulses.

As described in the above embodiments, the collecting position of the terahertz wave pulses may be moved by an actuator (not shown) provided on the side of the object to be measured. As such, since the generation unit 313 and the detection unit 314 are separated, an incident angle of the terahertz wave pulses incident on the object to be measured can be variable. An adjustable incident angle allows adjustment of a measurement region such that, for example, with an angle with respect to a vertical line (line substantially equal to a propagation direction of the terahertz waves incident on the object to be measured) of the object to be measured being defined as an incident angle, the incident angle is increased to obtain information on a surface of the object to be measured surface, and the incident angle is reduced to obtain information on a deep region of the object to be measured. The measurement region of the object to be measured can be limited to reduce reflected signals from unnecessary spots, and thus an increase in measurement accuracy can be expected. FIG. 3A is a variant of Embodiment 1, but may also be applied to Embodiment 2.

Embodiment 4

Another aspect for carrying out the idea of the present invention will be described with reference to the drawings. This embodiment is a variant of the above described embodiments. Specifically, this embodiment relates to the measurement apparatus described above applied to a tomography apparatus. Descriptions on the same components as those in the above description will be omitted.

A time axis of a time waveform of terahertz wave pulses can be converted into a distance. Thus, the time waveform of the terahertz wave pulses described above can be captured as an A-scan image of a tomographic image. Thus, an optical axis along which the terahertz wave pulses propagate can be moved to cross a direction of the terahertz wave pulses incident on the object to be measured to obtain a B-scan image or a three-dimensional tomographic image.

Figure 13:
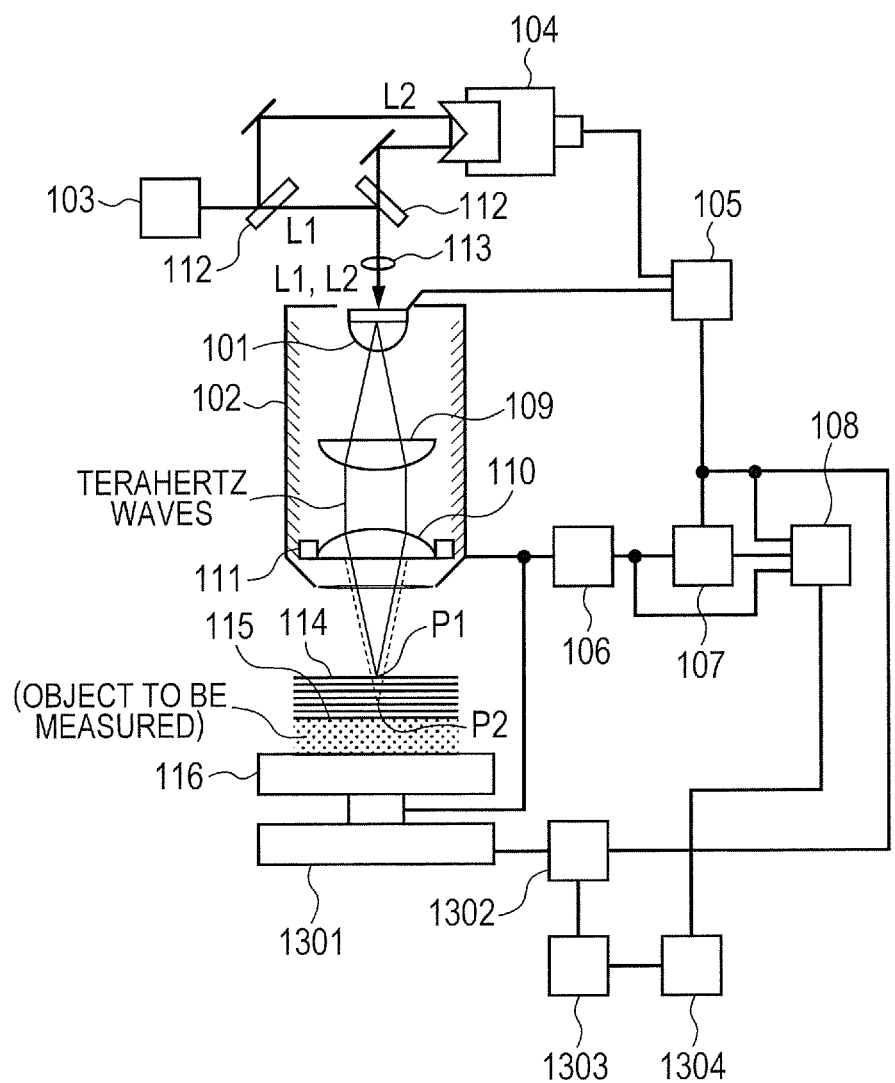
FIG. 13 is a schematic configuration diagram of an apparatus described in Embodiment 4.

FIG. 13 is a schematic configuration diagram of a tomographic image obtaining apparatus of this embodiment. Specifically, the measurement apparatus of Embodiment 1 is applied to the tomographic image obtaining apparatus. The measurement apparatus of Embodiment 2 or 3 can be similarly applied to the tomographic image obtaining apparatus. This apparatus includes, in addition to the apparatus configuration of Embodiment 1: a moving stage 1301 configured to relatively move positions of the object to be measured and the terahertz wave pulses; an image constructing unit 1302 configured to relate a position (observation point) of the moving stage 1301 to a time waveform output from a waveform obtaining unit 105 to construct a tomographic image of the object to be measured; a characteristic region extracting unit 1303 configured to extract a characteristic region from the tomographic image; and a correcting unit 1304 configured to calculate a thickness t and an average refractive index n(ave) by the apparatus configuration described above for the region extracted by the characteristic region extracting unit 1303, and correct the obtained tomographic image by the information.

The moving stage 1301 is placed on the side of the object to be measured. The moving stage 1301 moves the object to be measured so as to cross an application direction of the terahertz wave pulses. However, the position of the moving stage 1301 is not limited to this, such that otherwise the moving stage 1301 may be placed in a position for moving the optical axis of the terahertz wave pulses. Specifically, the moving stage 1301 may be a unit that can relatively move the object to be measured and the terahertz wave pulses so as to cross each other. The moving stage 1301 may also have a function of moving the collecting position of the terahertz wave pulses in the application direction of the terahertz wave pulses.

As described above, the image constructing unit 1302 relates information of the measured waveform by the waveform obtaining unit 105 to the position (also referred to as the observation point in this embodiment) of the moving stage 1301 to construct a desired tomographic image. The moving stage 1301 is moved in one direction to form a B-scan tomographic image. The moving stage 1301 is two-dimensionally moved to construct a three-dimensional tomographic image. The moving stage 1301 is two-dimensionally moved with the optical path length difference by the delay optical unit 104 being fixed to construct a C-scan tomographic image. The image constructing unit 1302 sometimes reconstructs and outputs a B-scan or C-scan tomographic image from the constructed three-dimensional tomographic image.

The characteristic region extracting unit 1303 extracts a characteristic region from the tomographic image constructed by the image constructing unit 1302. An operator refers to the tomographic image and selects a region of note as the characteristic region. Alternatively, the apparatus may refer to the B-scan or C-scan tomographic image to automatically detect and extract a position where an interface of the reflection portion is discontinuous. At this time, the discontinuous points may be connected to form a boundary, and an obtained image may be divided into some components and presented. The correcting unit 1304 uses the physical property obtaining unit 108 to calculate the average refractive index n(ave) and the thickness t for the selected characteristic region, and refers to the information to correct an obtained image. Specifically, the correcting unit 1304 adjusts a thickness of each characteristic region. With the configuration of Embodiment 2, the material of the characteristic region and the physical property of the material may be specified and displayed in a color-coded manner according to the specified information.

With reference to FIGS. 14, 15A, 15B, 16A and 16B, the operation of the tomographic image obtaining apparatus of this embodiment will be described. FIG. 14 is a typical operation flow relating to the apparatus of this embodiment. For the operation flow, descriptions on the same components as those in the above description will be omitted. This operation flow is described with an example of using skin as the object to be measured. However, the object to be measured is not limited to skin.

Figure 15A:
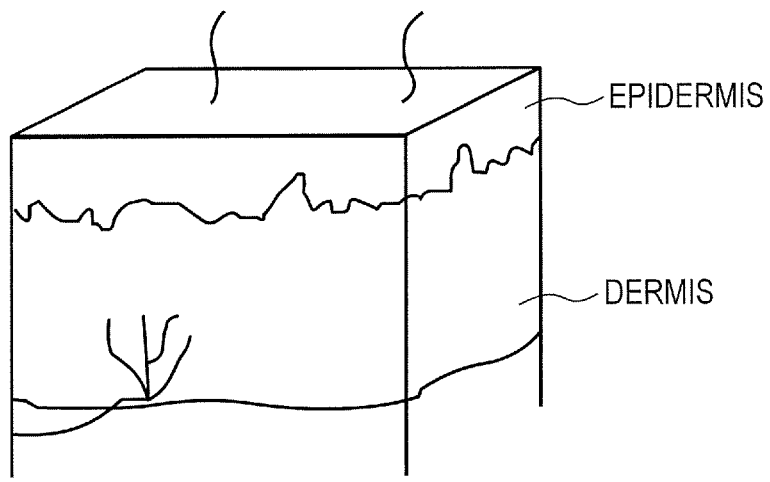
FIGS. 15A and 15B are schematic diagrams of skin.
Figure 15B:
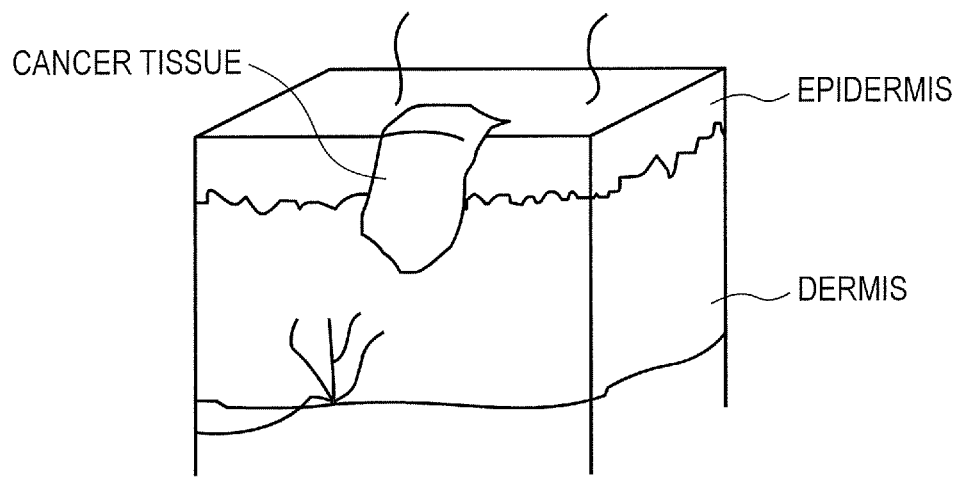

FIG. 15A is a schematic diagram of skin used as an object to be measured. As a typical structure of skin, epidermis has a thickness of several hundreds of μm and dermis has a thickness of several mm. The epidermis contains epidermal cells, pigment cells, and Langerhans cells, and it has keratin of a thickness of several tens of μm on an outermost surface. The dermis contains collagen and elastin. For example, the tomographic image obtaining apparatus of this embodiment images an outermost surface of the epidermis, a boundary between the epidermis and the dermis, and a boundary between the dermis and subcutaneous tissue. FIG. 15B is a schematic diagram when skin has cancer tissue. It is known that cancer tissue has higher moisture content than healthy tissue. Thus, a difference in moisture content can be imaged to identify cancer tissue. When a living body typified by skin is used as an object to be measured, it is difficult to obtain a tomographic image relating to a region at a depth of several mm to several tens of mm with accuracy of several tens of μm to several hundreds of μm because of high absorption or scattering of visible lights or infrared rays on the living body. Such a tomographic image can be obtained by an apparatus configuration that uses transmission of terahertz waves and increases measurement resolution with the terahertz waves in the form of pulses.

Figure 16A:
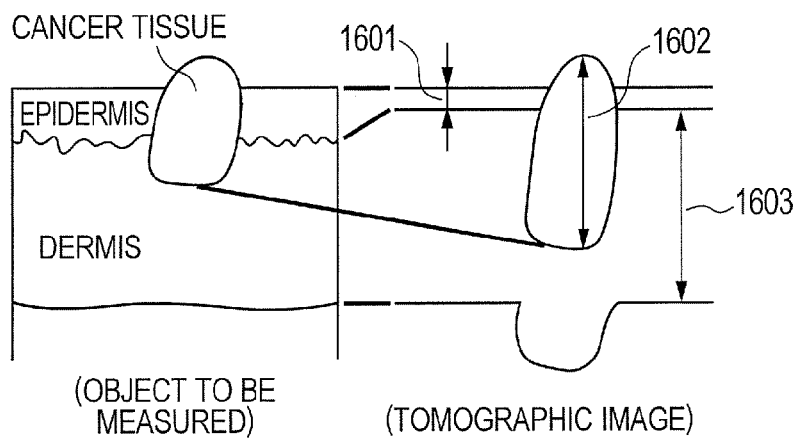
FIGS. 16A and 16B are schematic diagrams of an object to be measured and a tomographic image thereof.

In FIG. 14, when the tomographic image obtaining apparatus starts to operate, the apparatus obtains a tomographic image (S301). Specifically, the moving stage 1301 moves an observation point of terahertz wave pulses, and the waveform obtaining unit 105 obtains a time waveform of the terahertz wave pulses at each observation point. The image constructing unit 1302 uses a position of the observation point determined by the moving stage 1301 and the time waveform of the terahertz wave pulses at the observation point to construct a tomographic image. FIG. 16A is a schematic diagram of an object to be measured and a tomographic image thereof. A B-scan tomographic image is shown in FIG. 16A. A difference in physical property between areas that constitute the object to be measured causes a difference in propagation speed of the terahertz wave pulses, and thus causes a different optical length between the areas. As a result, as in the tomographic image in FIG. 16A, a position of an interface partially changes as compared to a section of the object to be measured.

For the constructed tomographic image, the characteristic region extracting unit 1303 selects a characteristic region (S302). For example, in FIG. 16A, a region between an outermost surface of epidermis and an interface between the epidermis and dermis as a characteristic region is a first characteristic point 1601. A region between an outermost surface of cancer tissue and an interface between the cancer tissue and the dermis is a second characteristic point 1602. A region between the interface between the epidermis and the dermis and an interface between the dermis and subcutaneous tissue is a third characteristic point 1603. The apparatus uses the moving stage 1301 in FIG. 13 and the actuator 116 to move an observation region of terahertz wave pulses to a characteristic region to be noted (S303).

Figure 16B:
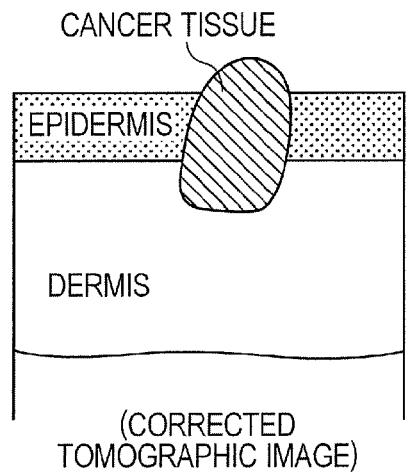

The steps S101 to S109 are used to calculate an average refractive index n(ave) and a thickness t of each observation point (S304). Physical properties of each characteristic region are obtained using the steps S202 to S204 (S305). Specifically, the physical properties are obtained to specify a material for the characteristic region. The correcting unit 1304 refers to the average refractive index n(ave) and the thickness t of each characteristic region to adjust an optical length of the obtained tomographic image (S306). This is shown in FIG. 16B. When materials for the characteristic regions can be specified, the characteristic regions are presented with different display manners depending on the materials. For example, the materials are presented in different colors.

According to the tomographic image obtaining apparatus of this embodiment, the material for the object to be measured is specified by the obtained information of the tomographic image. This can provide a tomography apparatus that can collect a change of the image by the physical property of the material, and specify a material for the corrected portion. For the same reason, a tomographic image obtaining method according to this embodiment can collect a change of the image by the physical property of the material, and specify a material for the corrected portion. In this embodiment, not limited to a case where terahertz waves (30 GHz to 30 THz) having a wavelength of 10 mm to 10 μm are used as electromagnetic wave pulses, electromagnetic waves having any wavelengths can be used in measuring an object to be measured having substantially the same size as the collimated region of the confocal optical system. Terahertz waves having a depth of focus (collimated region) of several mm may be desirably used. Not limited to the terahertz waves, for example, electromagnetic waves of a long waveform (low frequency) region such as microwaves having a wavelength of 1 m to 100 μm (frequency band of a 300 MHz to 3 THz), or centimeter waves having a wavelength of 10 mm to 100 mm (frequency band of 3 GHz to 30 GHz) may be used.

Now, specific examples will be described.

Example 1

An example of the apparatus configuration in Embodiment 3 is described. Descriptions on the same components as those in the above description will be omitted. In this example, photoconductive elements are used as the generation unit 313 and the detection unit 314. As a semiconductor film of the generation unit 313, low-temperature grown gallium indium arsenic (LT-GaInAs) is used. As a semiconductor film of the detection unit 314, low-temperature grown gallium arsenic (LT-GaAs) is used. A dipole antenna having a length of 20 μm and a width of 10 μm is patterned on each semiconductor film. The shaping unit 102 includes four parabolic mirrors.

The object to be measured is placed on the actuator 116, and a collecting position of the terahertz wave pulses is adjusted by the actuator 116. The collecting position adjusting unit 106 is a driver configured to control the actuator 116. The light source 103 uses a femtosecond fiber laser having a central wavelength of 1.56 μm, a pulse width of 30 femtoseconds, and a repetition frequency of 50 MHz. For an excitation light $L_2$, a wavelength conversion element (PPLN) is placed between the beam splitter and the delay optical unit 104 to obtain a femtosecond laser having a central wavelength of 0.78 μm and a pulse width of 70 femtoseconds. An excitation light $L_1$ of 20 mW is incident on the generation unit 313. An excitation light $L_2$ of 1 mW is incident on the detection unit 314. The delay optical unit 104 includes a direct-acting stage and a retroreflector. Position information of the direct-acting stage is input to the waveform obtaining unit 105. The waveform obtaining unit 105 includes a current amplifier and an A/D board. An output from the current amplifier corresponding to position information of the delay optical unit 104 is successively plotted to construct a time waveform of the terahertz wave pulses. The measurement position information obtaining unit 107 and the physical property obtaining unit 108 include a processor.

Figure 10A:
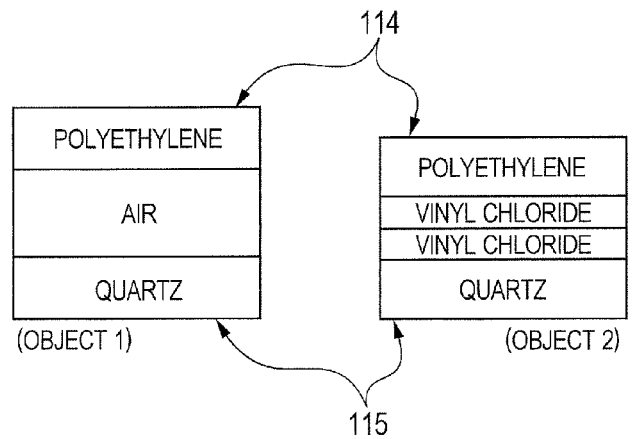
FIGS. 10A, 10B and 10C illustrate an object to be measured used in Example 1.

A configuration of the object to be measured used in this example is shown in FIG. 10A. Here, two objects to be measured are used. A stack of polyethylene and quartz via an air space is used as an object to be measured 1. A stack of polyethylene, vinyl chloride, and quartz is used as an object to be measured 2. An overall thickness of the object to be measured 1 is about 1.1 mm. An overall thickness of the object to be measured 2 is about 0.9 mm.

Figure 10B:
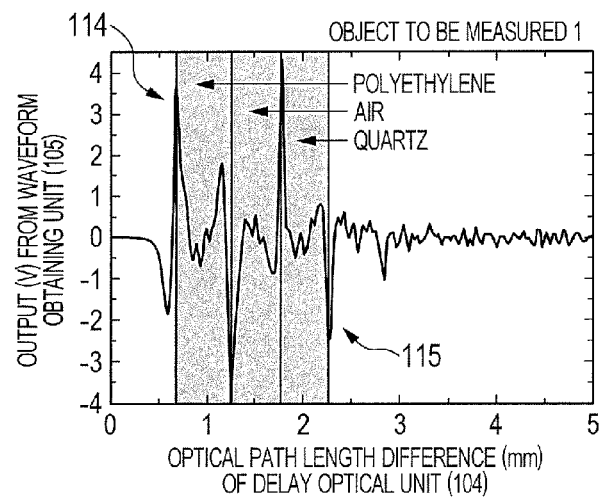
Figure 10C:
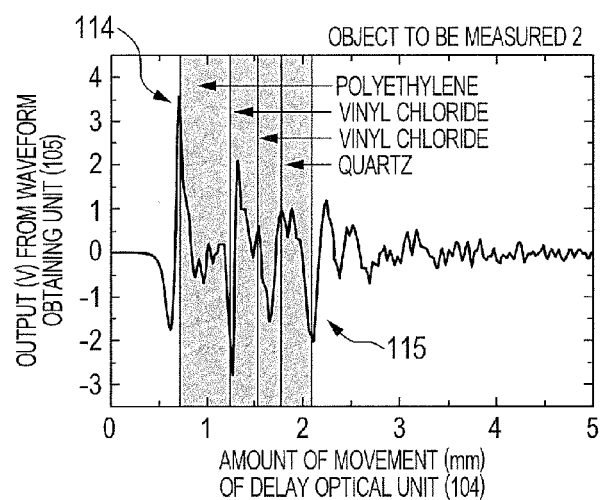

FIGS. 10B and 10C show time waveforms of the terahertz wave pulses from the objects to be measured obtained by the waveform obtaining unit 105. From the time waveforms, reflection pulses from four interfaces can be checked in the object to be measured 1 (FIG. 10B), and reflection pulses from five interfaces can be checked in the object to be measured 2 (FIG. 10C). In this example, the first interface is the first reflection portion 114, and the last interface is the second reflection portion 115.

Figure 11A:
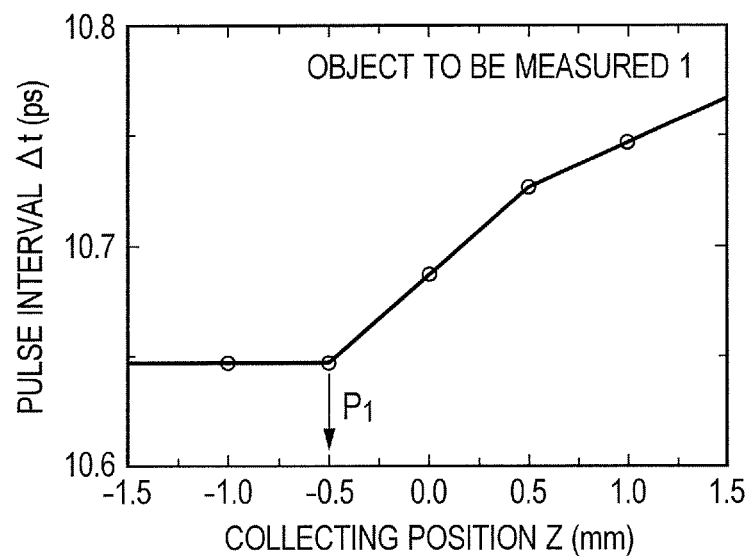
FIGS. 11A and 11B illustrate an operation of a measurement position information obtaining unit in Example 1.
Figure 11B:
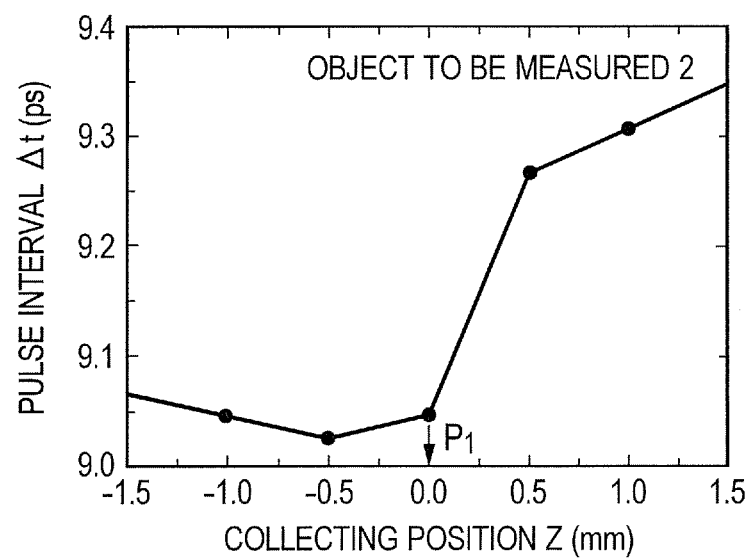

FIGS. 11A and 11B show an operation of the measurement position information obtaining unit 107. The collecting position is changed by moving the object to be measured. FIG. 11A relates to the object to be measured 1, and a change of a pulse interval for the collecting position similar to that in FIG. 7A can be checked. From FIG. 11A, an amount of adjustment of the collecting position Z where a pulse interval Δt tends to increase is determined as a position of the first reflection portion 114. FIG. 11B relates to the object to be measured 2, and a tendency similar to that of the object to be measured 1 can be checked.

Figure 12A:
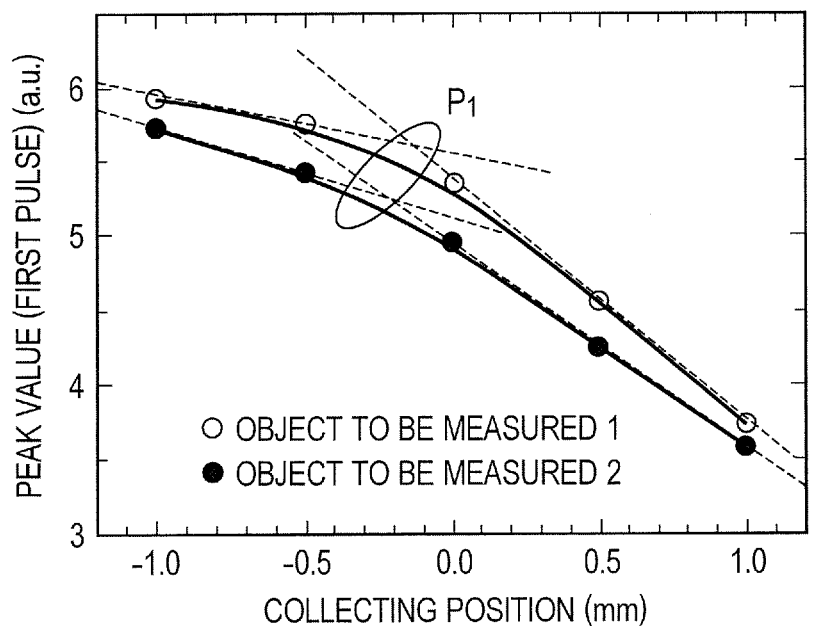
FIGS. 12A and 12B illustrate an operation of the measurement position information obtaining unit in Example 1.
Figure 12B:
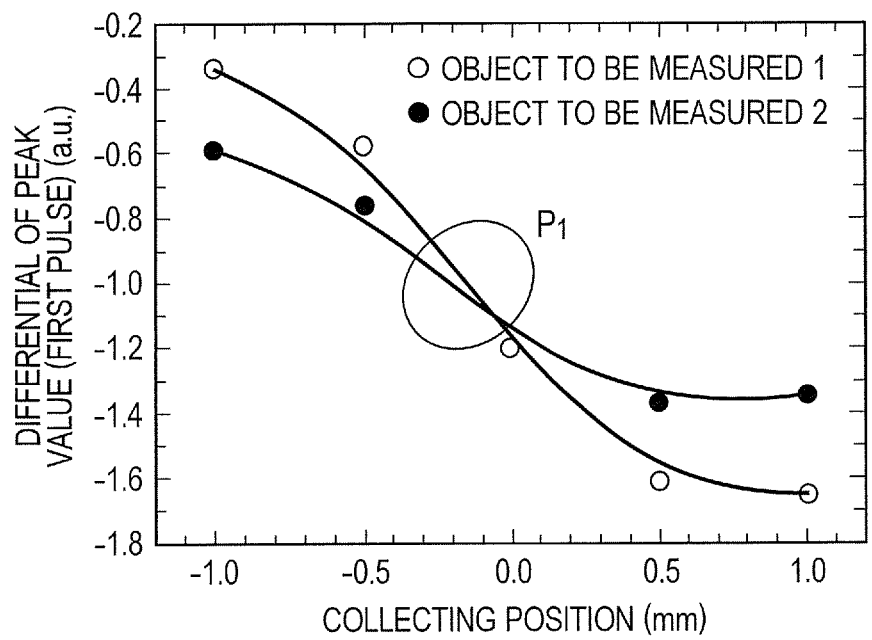

FIGS. 12A and 12B also show the operation of the measurement position information obtaining unit 107. In FIG. 12A, a change of a peak value for the collecting position similar to that in FIG. 7B can be checked. From FIG. 12A, an amount of adjustment of the collecting position Z where a gradient of a peak value changes is calculated from an asymptote for each object to be measured, and this is a position of the first reflection portion. In FIG. 12B, a change of a differential value of a peak value for the collecting position is similar to that in FIG. 7C. From FIG. 12B, an amount of adjustment of the collecting position Z where the gradient of the peak value changes is calculated from the point of change of the differential value for each object to be measured, and this is determined as a position of the first reflection portion 114. A position of the second reflection portion 115 is also calculated from the change of the peak value of the second pulse in the same manner.

In FIGS. 11A and 11B and FIGS. 12A and 12B, absolute amounts of the collecting position Z are partially different for the same object to be measured, and this is because of a difference in measurement method and a measurement condition (measurement position or placement of the object to be measured). As is apparent from Expression (1) to (4), the physical property obtaining unit 108 may only be required to ensure a relative relationship between the amount of movement $|Z_2-Z_1|$ by the collecting position adjusting unit 106 and the amount of movement $|D_2-D_1|$ by the delay optical unit 104, and thus the absolute amounts may be different.

In this example, the measurement position information obtaining unit 107 detects the reflection portion by the change of the pulse interval. Results of output from the measurement position information obtaining unit 107 and the physical property obtaining unit 108 at this time are shown in the table below.

TABLE 1

| | MEASUREMENT POSITION INFORMATION OBTAINING UNIT 107 | | | | PHYSICAL PROPERTY OBTAINING UNIT 108 | |
|---|---|---|---|---|---|---|
| | COLLECTING POSITION Z1 | OPTICAL PATH LENGTH DIFFERENCE D1 | COLLECTING POSITION Z2 | OPTICAL PATH LENGTH DIFFERENCE D2 | REFRACTIVE INDEX n | THICKNESS t |
| OBJECT TO BE MEASURED 1 | −0.5 mm | 2.1 mm | 0.5 mm | 2.79 mm | 1.28 | 1.26 mm |
| OBJECT TO BE MEASURED 2 | 0 mm | 1.69 mm | 0.5 mm | 2.58 mm | 1.65 | 0.81 mm |

The collecting position is adjusted by moving the object to be measured. Thus, calculation by the physical property obtaining unit 108 uses Expressions (1) and (2). In the expressions, sin θ as the number of apertures is 0.24. Further, an incident angle of the terahertz wave pulses with respect to the object to be measured is about 15°. Thus, when the physical property obtaining unit 108 calculates a thickness, correction with the incident angle is performed. It is apparent from the calculation result of the physical property obtaining unit 108 that the thickness is close to the previously measured thickness of each object to be measured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-047462, filed Mar. 4, 2012, which is hereby incorporated by reference herein in its entirety.

The invention claimed is:

1. A measurement apparatus configured to obtain a physical property of an object to be measured including a first reflection portion and a second reflection portion, comprising:
   a generating unit configured to generate electromagnetic wave pulses;
   a detection unit configured to detect the electromagnetic wave pulses from the object;
   a delay unit configured to adjust an optical path length difference between a light path length of a first excitation light reaching the generating unit and a light path length of a second excitation light reaching the detection unit, or a time difference between a timing when the first excitation light reaches the generating unit and a timing when the second excitation light reaches the detection unit;
   a shaping unit configured to collect the electromagnetic wave pulses on the object;

a waveform obtaining unit configured to refer to an output from the detection unit and an amount of adjustment of the delay unit to construct a time waveform of the electromagnetic wave pulses;

a collecting position adjusting unit configured to adjust a relative position between the object and a collecting position of the electromagnetic wave pulses collected by the shaping unit substantially along an optical axis of the electromagnetic wave pulses;

a measurement position information obtaining unit configured to obtain a first position information when an interface between a light collecting process region and a light collimated region of the electromagnetic wave pulses collected in the shaping unit matches the first reflection portion and a second position information when the interface matches the second reflection portion, based on a change of the time waveform obtained in the waveform obtaining unit with a change of the relative position; and a physical property obtaining unit configured to obtain a physical property of a region between the first reflection portion and the second reflection portion based on information of the first position information and the second position information obtained in the measurement position information obtaining unit.

2. A measurement apparatus configured to obtain a physical property of an object to be measured including a first reflection portion and a second reflection portion comprising:

a generating unit configured to generate electromagnetic wave pulses;

a detection unit configured to detect the electromagnetic wave pulses from the object;

a delay unit configured to adjust an optical path length difference between a light path length of a first excitation light reaching the generating unit and a light path length of a second excitation light reaching the detection unit, or a time difference between a timing when the first excitation light reaches the generating unit and a timing when the second excitation light reaches the detection unit;

a shaping unit configured to collect the electromagnetic wave pulses on the object;

a waveform obtaining unit configured to refer to an output from the detection unit and an amount of adjustment of the delay unit to construct a time waveform of the electromagnetic wave pulses; and a collecting position adjusting unit configured to adjust a relative position between the object and a collecting position of the electromagnetic wave pulses collected by the shaping unit substantially along an optical axis of the electromagnetic wave pulses, a measurement position information obtaining unit configured to obtain a position information of the first reflection portion and a position information of the second reflection portion, based on a change of the time interval of a first pulse from the first reflection portion and a second pulse from the second reflection portion in the time waveform obtained in the waveform obtaining unit with a change of the relative position; and a physical property obtaining unit configured to obtain a physical property of a region between the first reflection portion and the second reflection portion of the object based on a position information of the first reflection portion and a position information of the second reflection portion.

3. The measurement apparatus according to claim 1, further comprising:

a database that stores physical property information and a time waveform of electromagnetic wave pulses for each material;

a waveform adjusting unit configured to select, from the database, a candidate material for the region between the first reflection portion and the second reflection portion of the object by the refractive index, and adjust a time waveform of the candidate material to a time waveform including an influence of the calculated thickness and the stored physical property information;

a waveform comparing unit configured to compare the time waveform of the electromagnetic wave pulses constructed by the waveform obtaining unit with the time waveform from the waveform adjusting unit; and a physical property specifying unit configured to specify a material highly correlated with the constructed time waveform of the electromagnetic wave pulses from an output from the waveform comparing unit.

4. The measurement apparatus according to claim 1, further comprising:

a moving stage configured to move relative positions of the object and the collecting position in a direction crossing the optical axis; and an image constructing unit configured to relate the relative positions by the moving stage to a time waveform output from the waveform obtaining unit to construct a tomographic image of the object.

5. The measurement apparatus according to claim 2, further comprising:

a moving stage configured to move relative positions of the object and collecting position in a direction crossing the optical axis; and an image constructing unit configured to relate the relative positions by the moving stage to a time waveform output from the waveform obtaining unit to construct a tomographic image of the object.

6. The measurement apparatus according to claim 4, further comprising:

a characteristic region extracting unit configured to extract a characteristic region from the tomographic image; and a correcting unit configured to correct the constructed tomographic image by information of a thickness and a refractive index obtained by calculation for the region extracted by the characteristic region extracting unit.

7. The measurement apparatus according to claim 1, wherein the delay unit is a delay optical unit which adjusts an optical path length of the first excitation light or an optical path length of the second excitation light to adjust an optical path length difference, the first position information is an amount of adjustment $Z_1$ of the collecting position adjusting unit when the interface matches the first reflection unit, and an optical path length difference $D_1$ by the delay optical unit required for detecting the first pulse from the first reflection portion at the amount of adjustment $Z_1$, and the first position information is an amount of adjustment $Z_2$ of the collecting position adjusting unit when the interface matches the second reflection unit, and an optical path length difference $D_2$ by the delay optical unit required for detecting the second pulse from the second reflection portion at the amount of adjustment $Z_2$.

8. The measurement apparatus according to claim 7, wherein the physical property obtaining unit is configured to obtain a thickness and a refractive index of the region based on an amount of change $|Z_2-Z_1|$ of an amount of adjustment by the collecting position adjusting unit and an amount of change $|D_2-D_1|$ of an optical path length difference by the delay optical unit.

9. The measurement apparatus according to claim 1, wherein the delay unit adjusts a timing when the first excitation light reaches the generating unit and a timing when the second excitation light reaches the detection unit to adjust the time difference, the first position information is an amount of adjustment $Z_1$ of the collecting position adjusting unit when the interface matches the first reflection unit, and an optical path length difference $D_1$ converted from the time difference by the delay unit required for detecting the first pulse from the first reflection portion at the amount of adjustment $Z_1$, and the first position information is an amount of adjustment $Z_2$ of the collecting position adjusting unit when the interface matches the second reflection unit, and an optical path length difference $D_2$ converted from the time difference by the delay unit required for detecting the second pulse from the second reflection portion at the amount of adjustment $Z_2$.

10. The measurement apparatus according to claim 9, wherein the physical property obtaining unit is configured to obtain a thickness and a refractive index of the region based on an amount of change $|Z_2-Z_1|$ of an amount of adjustment by the collecting position adjusting unit and an amount of change $|D_2-D_1|$ of an amount of an optical path length difference by the delay optical unit.

11. The measurement apparatus according to claim 1, wherein the measurement position information obtaining unit is configured to obtain a position information of the first reflection portion and position information of the second reflection portion, based on a change of a time interval of a first pulse from the first reflection portion and a second pulse from the second reflection portion in the time waveform obtained in the waveform obtaining unit with a change of the relative position.

12. The measurement apparatus according to claim 1, wherein the measurement position information obtaining unit is configured to obtain a position information of the first reflection portion and position information of the second reflection portion, based on a change of a time interval of a peak value of a first pulse from the first reflection portion and a peak value of a second pulse of the second reflection portion in the time waveform obtained in the waveform obtaining unit with a change of the relative position.

13. The measurement apparatus according to claim 2, further comprising:
a database that stores physical property information and a time waveform of electromagnetic wave pulses for each material;
a waveform adjusting unit configured to select, from the database, a candidate material for the region between the first reflection portion and the second reflection portion of the object by the refractive index, and adjust a time waveform of the candidate material to a time waveform including an influence of the calculated thickness and the stored physical property information;
a waveform comparing unit configured to compare the time waveform of the electromagnetic wave pulses constructed by the waveform obtaining unit with the time waveform from the waveform adjusting unit; and
a physical property specifying unit configured to specify a material highly correlated with the constructed time waveform of the electromagnetic wave pulses from an output from the waveform comparing unit.

14. The measurement apparatus according to claim 2, wherein the delay unit is a delay optical unit configured to adjust a light path length of a first excitation light or a light path length of a second excitation light to adjust the light path length, the first position information is an amount of adjustment $Z_1$ of the collecting position adjusting unit when an interface of a light collecting process region of the electromagnetic wave pulse and the collimated region matches the first reflection unit, and an optical path length difference $D_1$ by the delay optical unit required for detecting the first pulse from the first reflection portion at the amount of adjustment $Z_1$, and the first position information is an amount of adjustment $Z_2$ of the collecting position adjusting unit when the interface matches the second reflection unit, and an optical path length difference $D_2$ by the delay optical unit required for detecting the second pulse from the second reflection portion at the amount of adjustment $Z_2$.

15. The measurement apparatus according to claim 14, wherein the physical property obtaining unit is configured to obtain a thickness and a refractive index of the region based on an amount of change $|Z_2-Z_1|$ of an amount of adjustment by the collecting position adjusting unit and an amount of change $|D_2-D_1|$ of an amount of an optical path length difference by the delay optical unit.

16. The measurement apparatus according to claim 2, wherein the delay unit adjusts a timing when the first excitation light reaches the generating unit and a timing when the second excitation light reaches the detection unit to adjust the time difference, the first position information is an amount of adjustment $Z_1$ of the collecting position adjusting unit when the interface matches the first reflection unit, and an optical path length difference $D_1$ converted from the time difference by the delay unit required for detecting the first pulse from the first reflection portion at the amount of adjustment $Z_1$, and the first position information is an amount of adjustment $Z_2$ of the collecting position adjusting unit when the interface matches the second reflection unit, and an optical path length difference $D_2$ converted from the time difference by the delay unit required for detecting the second pulse from the second reflection portion at the amount of adjustment $Z_2$.

17. The measurement apparatus according to claim 16, wherein the physical property obtaining unit is configured to obtain a thickness and a refractive index of the region based on an amount of change $|Z_2-Z_1|$ of an amount of adjustment by the collecting position adjusting unit and an amount of change $|D_2-D_1|$ of an amount of an optical path length difference by the delay optical unit.

18. The measurement apparatus according to claim 5, further comprising:
a characteristic region extracting unit configured to extract a characteristic region from the tomographic image; and
a correcting unit configured to correct the constructed tomographic image by information of a thickness and a refractive index obtained by calculation for the region extracted by the characteristic region extracting unit.

19. A measurement method for obtaining a physical property of an object including a first reflection portion and a second reflection portion, comprising:
a generating step of generating electromagnetic wave pulses in a generation unit;

a detecting step of detecting the electromagnetic wave pulses from the generation unit in a detection unit;

a delaying step of adjusting an optical path length difference between a light path length of a first excitation light reaching the generating unit and a light path length of a second excitation light reaching the detection unit, or a time difference between a timing when the first excitation light reaches the generating unit and a timing when the second excitation light reaches the detection unit;

a shaping step of collecting the electromagnetic wave pulses on the object;

a waveform obtaining step of constructing a time waveform of the electromagnetic wave pulses by referring to an output in the detecting step and an amount of adjustment in the delaying step;

a collecting position adjusting step of adjusting a relative position between the object and a collecting position of the electromagnetic wave pulses collected by the shaping unit substantially along an optical axis of the electromagnetic wave pulses;

a measurement position information obtaining step of obtaining a first position information when an interface between a light collecting process region and a light collimated region of the electromagnetic wave pulses collected in the shaping step matches the first reflection portion, and a second position information when the interface matches the second reflection portion, based on a change of the time waveform obtained in the a waveform obtaining step with a change of the relative position; and a physical property obtaining step of obtaining a physical property of a region between the first reflection portion and the second reflection portion based on an information of the first position information and the second position information obtained in the measurement position information obtaining step.

20. A measurement method for obtaining a physical property of an object to be measured including a first reflection portion and a second reflection portion, comprising:

a generating step of generating electromagnetic wave pulses in a generation unit;

a detecting step of detecting the electromagnetic wave pulses from the generation unit in a detection unit;

a delaying step of adjusting an optical path length difference between a light path length of a first excitation light reaching the generating unit and a light path length of a second excitation light reaching the detection unit, or a time difference between a timing when the first excitation light reaches the generating unit and a timing when the second excitation light reaches the detection unit;

a shaping step of collecting the electromagnetic wave pulses on the object;

a waveform obtaining step of constructing a time waveform of the electromagnetic wave pulses by referring to an output in the detecting step and an amount of adjustment in the delaying step;

a collecting position adjusting step of adjusting a relative position between the object and a collecting position of the electromagnetic wave pulses collected by the shaping unit substantially along an optical axis of the electromagnetic wave pulses;

a measurement position information obtaining step of obtaining a position information of the first reflection portion and a position information of the second reflection portion, based on a change of the time interval of a first pulse from the first reflection portion and a second pulse from the second reflection portion in the time waveform obtained in the waveform obtaining unit with a change of the relative position; and a physical property obtaining step of obtaining a physical property a region between the first reflection portion and the second reflection portion of the object based on a position information of the first reflection portion and a position information of the second reflection portion.

* * * * *